(12) United States Patent
Redwine et al.

(10) Patent No.: US 6,393,621 B1
(45) Date of Patent: May 28, 2002

(54) UNDERGARMENT FOR USE WITH AN ABSORBENT ARTICLE

(75) Inventors: Nona Jane Redwine, Mason; Deborah Catherine Schmitz, West Chester; Nicholas Albert Ahr, Cincinnati; Jerry Edward Carstens, West Chester; Ronald Bosman Visscher, Glendale, all of OH (US); Yuka Furutani, Nishinomiya (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/554,482

(22) PCT Filed: Nov. 9, 1998

(86) PCT No.: PCT/US98/23860

§ 371 (c)(1),
(2), (4) Date: May 15, 2000

(87) PCT Pub. No.: WO99/25298

PCT Pub. Date: May 27, 1999

(51) Int. Cl.[7] .................................................. A41C 1/00
(52) U.S. Cl. ............................................. 2/406; 2/400
(58) Field of Search ................ 2/400–408; 450/99–106; 604/385.01–396

(56) References Cited

U.S. PATENT DOCUMENTS

| | | | | |
|---|---|---|---|---|
| 2,205,745 A | * | 6/1940 | Fridolph | 450/100 |
| 2,792,698 A | * | 5/1957 | Hampp | 2/406 |
| 2,928,397 A | * | 3/1960 | Pucci | 450/100 |
| 3,368,563 A | * | 2/1968 | Scheier | 2/406 |
| 4,400,832 A | * | 8/1983 | Kinde | 2/406 |
| 4,527,403 A | * | 7/1985 | Fullbright et al. | 66/177 |
| 5,611,722 A | * | 3/1997 | Osborne | 450/99 |
| 5,888,118 A | * | 3/1999 | Kishi | 450/122 |

* cited by examiner

Primary Examiner—Gloria M. Hale
(74) Attorney, Agent, or Firm—Jeffrey V. Bamber; Kevin C. Johnson

(57) ABSTRACT

The present invention relates to undergarments that have close body fit. The undergarment of the present invention includes an elasticized waistband, a front region, a rear region, a crotch region and a pair of elasticized leg openings. The front and rear regions are preferably elastically extensible in both the longitudinal and lateral directions. The crotch region is disposed between the front and rear regions and has greater resistance to stretching in the longitudinal direction than the front and rear regions. The crotch region is further provided with a longitudinal stretch control member that is disposed along the longitudinal centerline of the undergarment and a plurality of angled stretch control members that extend from the longitudinal stretch control member to the leg elastics at an acute angle to the longitudinal stretch control member. The stretch control members limit the stretch of the crotch region in both the longitudinal and the lateral directions that causes the crotch region to conform to a wearer's skin surface. The rear region is provided with a lifting member that cooperates with the rear region, the front region and the longitudinal stretch control member to provide a "z-direction" biasing force along the longitudinal stretch control member. This biasing force, which is greater than the body contact force in adjacent portions of the crotch region, causes the crotch region, and any absorbent article that may be disposed thereon, to be lifted into close bodily contact when the undergarment is worn.

16 Claims, 14 Drawing Sheets

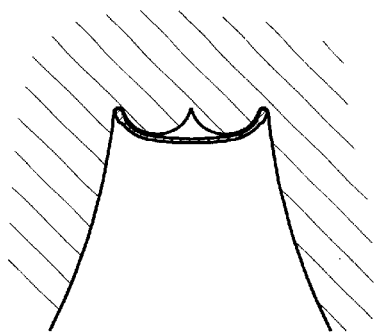
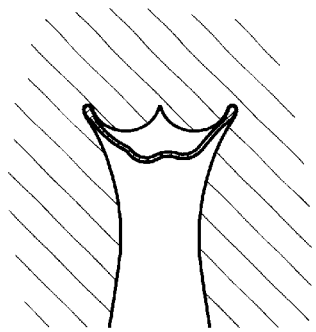
Fig. 3
Prior Art
Fig. 4
Prior Art
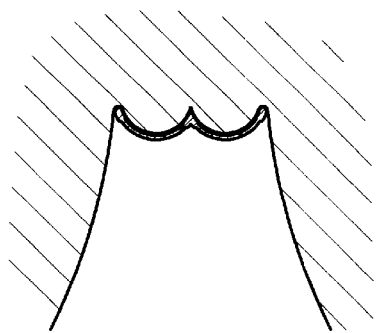
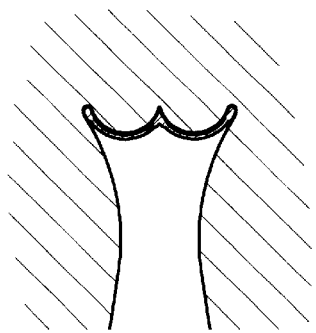
Fig. 5
Fig. 6

UNDERGARMENT FOR USE WITH AN ABSORBENT ARTICLE

FIELD OF THE INVENTION

The present invention relates to undergarments, particularly to undergarments that can be used in conjunction with an absorbent article, and more particularly to undergarments a user can wear with a catamenial device during her menstrual period.

BACKGROUND OF THE INVENTION

As is known, disposable catamenial devices are commercially available in a wide variety of configurations for the specific purpose of absorbing and retaining menstrual fluids and other vaginal discharges. Unfortunately, such catamenial devices may leak menses along their periphery due to poor fit or improper placement. Such leakage frequently results in soiling of a wearer's undergarments, clothing or bedding.

To provide additional protection against leakage, it is known to use a washable and reusable garment, such as a menstrual short or panty, in combination with a disposable catamenial pad. For example, U.S. Pat. No. 3,489,149, issued to Larson on Jan. 13, 1970, discloses a washable menstrual panty having a small pocket in the crotch area for retaining a disposable catamenial pad. Since the menses must initially flow through a layer of material forming the pocket to reach the catamenial pad, removal of the soiled catamenial pad can be distasteful, difficult and unsanitary. While a new pad can be inserted into the pocket, the garment is already soiled and would typically be changed. Also, the pocket may not accommodate the varied sizes of catamenial devices currently on the market. Further, the layer of moisture resistant material described therein fails to provide ventilation or breathability in the crotch region with a resulting potential for wearer discomfort when such a panty is worn.

The art has also attempted to address leakage from a catamenial device by providing absorbent material in a region surrounding the device and means for positioning the catamenial device. For example, U.S. Pat. No. 4,560,381, issued to Southwell on Dec. 24, 1985, describes a mesh-like outer panty shell with a thick inner layer of absorbent material in the lower crotch area of the panty. The inner layer of absorbent material includes a depression for receiving and positioning a catamenial pad. An alternative embodiment includes a barrier film between the absorbent material and the panty shell. However, if the barrier film is present, the crotch portion will not be breathable (with resulting discomfort) and if the barrier film is absent, there is a risk of leakage.

In U.S. Pat. No. 4,813,950, issued to Branch on Mar. 21, 1989, a washable menstrual panty is disclosed as having an outer lining of spandex, soft tricot, etc. which provides a "skin tight or almost skin tight" fit and an inner lining of a microporous plastic film to prevent passage of menses therethrough while allowing passage of gasses. Similarly, existing Japanese-style menstrual shorts act like a girdle or a very tight fitting panty which attempts to hold a catamenial device in the wearer's pudendal region. However. the tight fit of such undergarments has been reported to be uncomfortable to wearers and there is no apparent provision for directly lifting a catamenial device to a position close to a wearer's pudendal area.

A menstrual short panty having an elastic piece fixed to the front and rear of the crotch region in an elongated state is described in U.S. Pat. No. 3,608,551, issued to Seijo on Sep. 28, 1971. The elastic piece is said to keep a sanitary napkin raised and in contact with "the private parts of a human female's body irrespective of her physical movements . . . . " The elastic piece is joined to the leg openings by an open mesh network and the crotch region underlies the network. While such a device may improve body contact along a coronal centerline of a wearer's body, the device is unlikely to lift a catamenial absorbent into conformity with the external surface of a wearer's labia. Further. the narrow central elastic piece may cause the device to be uncomfortable to wearers because all of the lifting force appears to be concentrated along the wearer's coronal centerline.

Japanese Utility Model 4-9222, published in the name of Kao Corp. on Aug. 11, 1992 describes an undergarment having portions with differing mechanical properties wherein the fabric comprising the front part, the crotch part and the back central part has a longitudinal tensile strength that is at least twice the longitudinal tensile strength of the left and right back parts. With the tensile strength in the lateral direction being less than the tensile strength in the longitudinal direction in each of the parts. The undergarment is said to expand and shrink in accordance with wearer movement so a sanitary napkin disposed thereon will not shift. While such a garment may improve contact between the garment and a sanitary napkin disposed thereon, such improved contact will not, of necessity, provide improved body contact. Importantly, the consistent nature of the mechanical properties of the fabric that makes up the front part, the crotch part, and the back central part means that the garment is likely to provide an essentially constant force throughout the crotch part.

U.S. Pat. No. 5.611,722, issued to Osborn on Mar. 18, 1997 describes a panty-type undergarment. The panty-type undergarment has a front panel, a rear panel, and a crotch portion. The undergarment further includes a substantially anchor-shaped support panel having a greater resistance to stretch than the rest of the undergarment which is integrally knit into the rear panel. The support panel is said to lift and separate the cheeks of a wearer's buttocks. The support panel includes a vertical strip and upwardly curving portions which extend toward and along a portion of the undergarmnent's leg openings. While such undergarments may lift and separate the cheeks of a wearer's buttocks, the undergarments fail to provide a lifting force that would improve bodily contact between a catamenial device and a wearer's pudendal region.

Disposable menstrual panties are also known. For example PCT Application WO 95/06451 published in the name of Kimberly-Clark Corporation on Mar. 9, 1995 describes a disposable menstrual panty said to provide backup leakage protection by way of an absorbent/barrier composite positioned in the crotch area of the panty. The menstrual panty described therein is also provided with circumferentially oriented elastics said to allow the panty to conform to various body types and builds. However, because they only encircle a wearer's waist and hip areas, such elastics provide no "z direction" (i.e. upward) biasing force to help maintain a catamenial device in contact with a wearer's pudendal region. As a result. there is a risk of leakage around the catamenial device and a resultant risk of soiled outer garments or bedding.

It is therefore an object of the present invention to provide an undergarment that conforms to the external surfaces or a wearer's pudendal region without causing substantial discomfort. It is another object of the present invention to provide an undergarment that fits against a wearer's body so closely that it is like a "second skin". It is a further object of the present invention to provide an improved undergarment for use with a catamenial device or an incontinence control device which causes such devices to conform to the external surfaces of a wearer's pudendal region so as to provide improved protection against leakage. It is still a further object of the present invention to provide an undergarment which provides a biasing force to help insure close contact between such devices and a wearer's pudendal region throughout the full range of wearer motions without causing any significant wearer discomfort.

These and various other objectives of the present invention will be more readily apparent when considered in reference to the following description and when taken in conjunction with the accompanying drawings.

SUMMARY OF THE INVENTION

The present invention relates to undergarments that have close, almost "second skin," body fit. In particular the undergarments of the present invention are particularly well suited for helping hold an absorbent article, such as a catamenial pad or incontinence device, in close bodily contact throughout a wide range of wearer motions.

The undergarment of the present invention comprises an elasticized waistband, a front panel, a rear panel, a crotch panel and a pair of elasticized leg openings. The front and rear panels are preferably extensible in both the longitudinal and lateral directions. The crotch panel is disposed between the front and rear panels and has greater resistance to stretching in either of the longitudinal or lateral directions than the front and rear panels.

The rear panel is provided with a lifting member which cooperates with the rear panel to provide a "z-direction" biasing force along the longitudinal centerline of the undergarment. This biasing force causes the crotch panel, and any absorbent article that may be disposed thereon, to be lifted into close bodily contact when the undergarment is worn.

The crotch panel is further provided with a longitudinal stretch control member that is disposed along the longitudinal centerline of the undergarment and, preferably, a plurality of angled stretch control members that extend from the longitudinal stretch control member to the leg elastics at an acute angle to the longitudinal stretch control member. The longitudinal stretch control member directs forces from the front and rear panels so as to lift the crotch panel into close bodily contact along a sagittal centerline and the leg elastics lift the distal edges to close bodily contact adjacent a wearer's leg creases. As a result the crotch panel maintains close bodily contact over substantially the entire external surface of a wearer's labia. The ratio of the "z-direction" biasing force along the centerline to a body contact force on a labial surface is greater than 1:1.

While the undergarment of the present invention can be assembled from materials that may be known to the art as having the requisite mechanical properties, it is preferably knit. When the undergarment of the present invention is knit, the mechanical properties of the various components thereof can be provided by a combination of the knit pattern used for a particular component and the yams that are used. In a particularly preferred embodiment of the present invention, the stretch control members are integrally knit with the crotch panel and the lifting member is integrally knit with the rear panel.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying examples and drawings in which:

FIG. 3 is a schematic partial coronal cross section showing the crotch region of a prior art conventional undergarment during wear with the wearer's legs apart.

FIG. 4 is a schematic partial coronal cross section showing the crotch region of a prior art conventional undergarment during wear with the wearer's legs together.

FIG. 5 is a schematic partial coronal cross section showing the crotch region of the undergarment of the present invention undergarment during wear with the wearer's legs apart.

FIG. 6 is a schematic partial coronal cross section showing the crotch region of the undergarment of the present invention during wear with the wearer's legs together.

DETAILED DESCRIPTION OF THE INVENTION

The present invention relates to undergarment garments, more specifically to undergarments suitable for holding a disposable absorbent article in close contact with a wearer's body. A particularly preferred form of the present invention relates to an undergarment intended for use with catamenial devices, such as sanitary napkins, panty liners, and the like. to hold such devices in close body contact to help reduce the leakage from such devices. It should be understood, however, that the present invention is also applicable for use not only with catamenial devices but also other absorbent articles such as such devices. It should be understood, however, that the present invention is also applicable for use not only with catamenial devices but also other absorbent articles such as incontinence devices, particularly devices intended for wearers suffering from urinary incontinence, diaper inserts, and the like.

As used herein, the term "catamenial device" refers to an absorbent article which is worn by females adjacent to the pudendal region for absorbing and containing bodily fluids, such as menstrual fluids and other vaginal discharges. Also as used herein, the term "disposable" refers to structures which are not intended to be laundered or otherwise restored or reused after use (i.e., they are intended to be discarded after a single use, and, preferably, to be recycled, composted or otherwise disposed of in an environmentally compatible manner). As used herein, the term "pudendal" refers to the externally visible female genitalia and is limited to the labia majora, the labia minora, the clitoris and the vaginal vestibule. In addition, the term "perineum" refers to the external region of the female's body between the anus and the pudendal region while the term "gluteal groove" refers to the crevice between the buttocks (gluteus maximi) extending upwardly from the perineum. As used herein, the terms "fluid", "liquid" and the like are intended to be interchangeable and refer to materials that are in a liquid state when they are at a temperature of about 100° F. (38° C.).

General Description of the Undergarment

Figure 1:
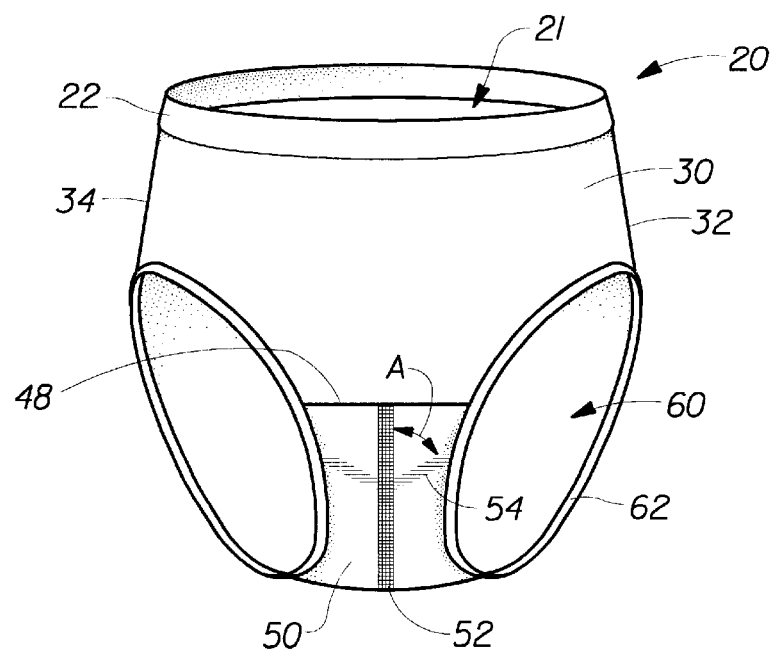
FIG. 1 is a front view of a preferred embodiment of the menstrual undergarment of the present invention.
Figure 2:
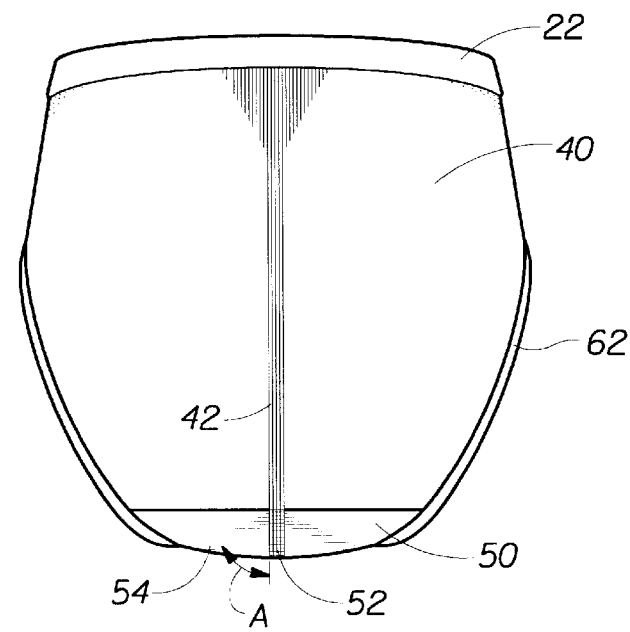
FIG. 2 is a rear view of the menstrual undergarment shown in FIG. 1.

While, as noted above, the present invention is suitable for use with a wide variety of absorbent articles, it will be described in terms of a menstrual undergarment 20 which may be used in conjunction with a catamenial device 200. FIGS. 1 and 2 show front and rear views of the menstrual undergarment 20 of the present invention. As is shown in FIGS. 1 and 2, the menstrual undergarment 20 of the present invention comprises a front region, such as front panel 30; a rear region, such as rear panel 40; a crotch region, such as, crotch panel 50; a pair of elasticized leg openings 60, and an elasticized waistband 22. The front panel 30 and the rear panel 40 are extensible in at least the longitudinal direction. The crotch panel 50 is extensible in at least the lateral direction. As used herein, a material is "extensible" if, when an external force is applied thereto, the material lengthens in the direction of the applied force and which will recover, upon release of the applied force, at least about 10 percent of its elongation.

The menstrual undergarment 20 is also provided with a waist opening 21 allowing entry into the menstrual undergarment 20. The menstrual undergarment 20 further comprises the crotch panel 50, and, preferably, a plurality of angled stretch control members 54 disposed at an angle A with respect to the longitudinal stretch control member 52 and extending therefrom to the leg elastics 62. It should be noted that the front edge 48 of the crotch panel 50 is preferably situated so that it lies under or behind (i.e. rearward of) a wearer's pubic bone so that the pubic bone does not interfere with the fit of the menstrual undergarment 20. Each of these elements will be described in greater detail in the following sections.

As noted above, one of the objects of the present invention is to provide an undergarment that fits against a wearer's body, particularly the pudendal area thereof, so closely that it is like a "second skin". FIGS. 3 to 6 schematically compare the fit of a conventional prior art undergarment in the crotch region when the wearer's legs are apart, and when they are brought together with the fit of the menstrual undergarment 20 of the present invention. A similar comparison is shown photographically in FIGS. 7–10.

Figure 9:
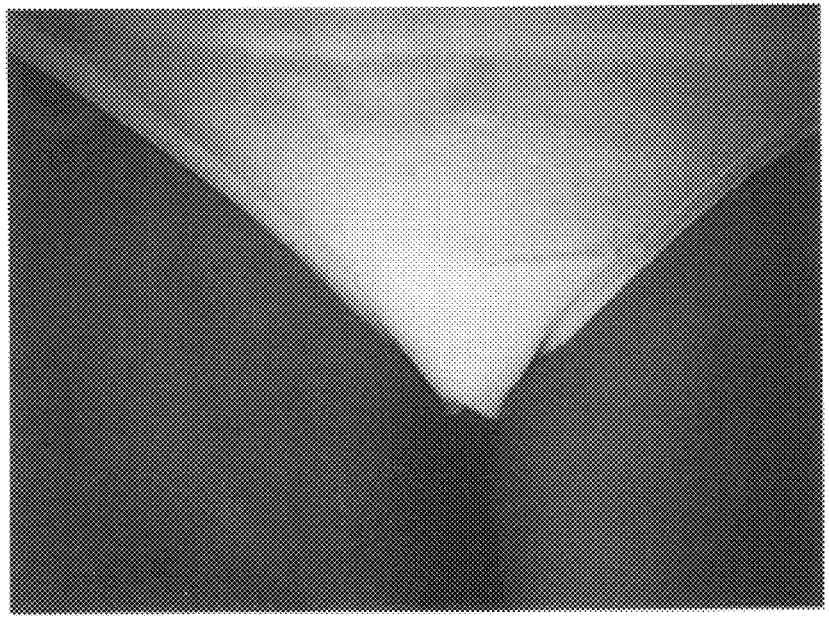
FIG. 9 is a frontal photograph of a conventional knit undergarment of the prior art with the wearer's legs closed.

As shown in FIGS. 3 and 9, the crotch region of such a conventional undergarment sags when the wearer's legs are brought together. As shown in FIG. 4, when the wearer's legs move apart, the crotch region of the conventional undergarment "gaps" or spans a longitudinally oriented area centered about the space between the wearer's labia. While FIG. 10 does not clearly show such gapping, the lack of close body contact when the wearer's legs are spread is obvious.

On the other hand, the menstrual undergarment 20 of the present invention, as shown in FIGS. 5, 6, 7, and 8. comfortably fits against and conforms to the outside surfaces of the labia majora whether the wearer's legs are apart, or together. As shown in FIGS. 5 and 6. in schematic partial coronal cross-section, the menstrual undergarment of the present invention maintains a modified cusp-shaped configuration in this area throughout a range of body motions. The cross-sectional configuration of the menstrual undergarment is described as being a "modified" cusp-shape because it may, but preferably does not form a point where the curved portions meet in the longitudinally oriented area at the space between the wearer's labia, but is more rounded, and preferably convex in this area. Similarly, FIGS. 7 and 8 demonstrate this modified cusp configuration in that the longitudinal stretch control member clearly remains disposed between the distal ends of the wearer's labia whether her legs are close together or spread (i.e. there is some penetration into the labial cleft).

Figure 11:
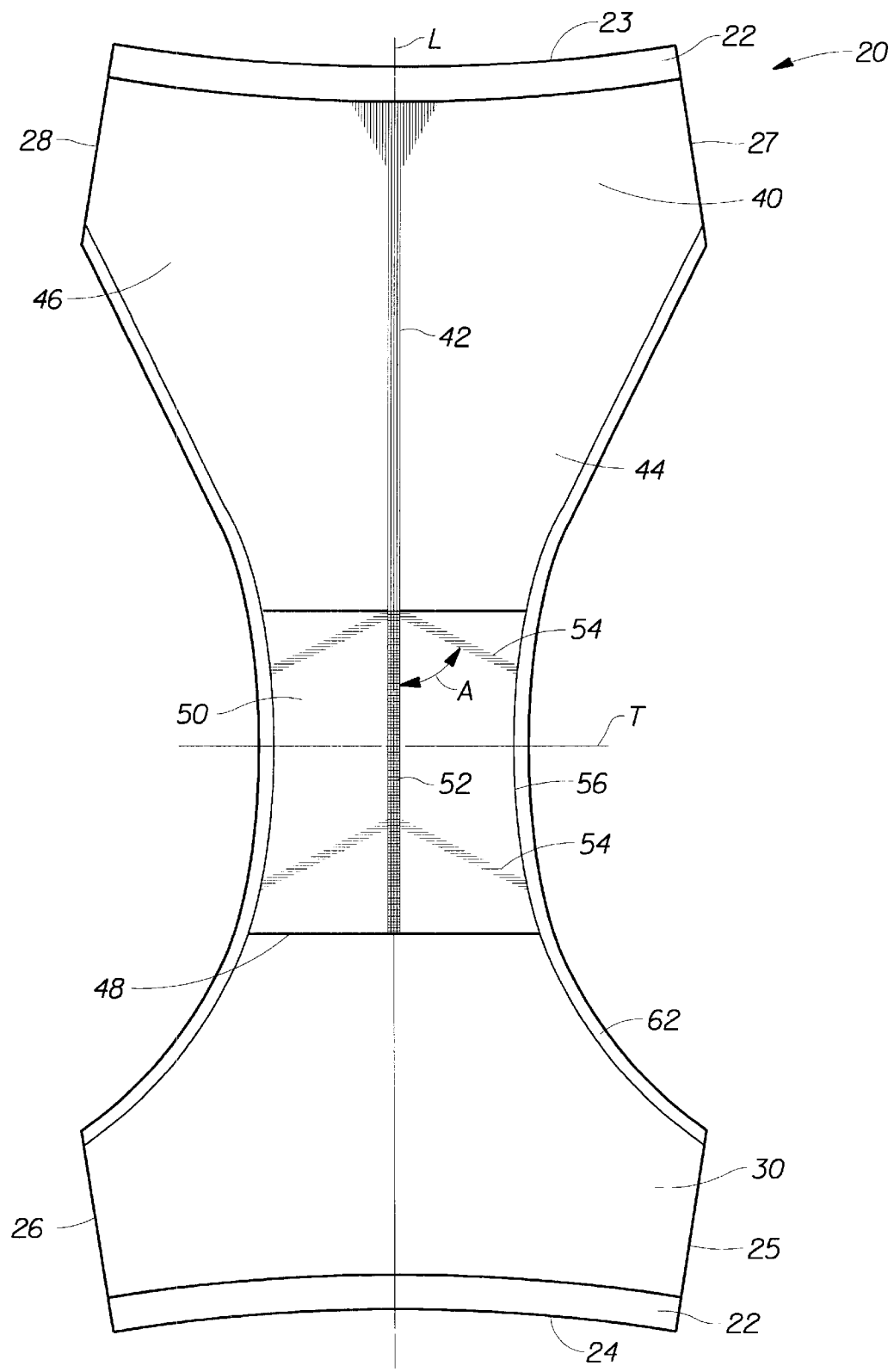
FIG. 11 is a plan view of the menstrual undergarment shown in FIG. 1 that has been opened at the side seams, the elastic components being pulled flat.

FIG. 11 shows the menstrual undergarment 20 of the present invention in a full flat out position wherein each of the side seams 32, 34 has been opened and elastic components have been pulled flat. FIG. 11 can also be considered to be a plan view of a blank for the menstrual undergarment 20 (see Forming the Undergarment below). As can be seen from FIG. 11, the menstrual undergarment 20 has a longitudinal centerline L and a transverse centerline T. As is also shown clearly in FIG. 11, the menstrual undergarment 20 of the present invention is symmetric about the longitudinal axis L and asymmetric about the transverse axis T. While not being bound by theory, it is believed that this transverse asymmetry enables the leg elastics 62 to provide a force which causes the crotch panel 50 curve upwardly over the external surface of a wearer's labia when the menstrual undergarment 20 is worn. It is further understood that co-operation between the leg elastics 62 and the angled stretch control members 54 provides the crotch panel 50 with resistance to narrowing on application of a longitudinally directed force resulting in a reduction in relative motion between the crotch panel 50 and a wearer's labia caused by wearer movement.

The menstrual undergarment 20 can comprise woven, nonwoven or knit fabrics. Preferably the menstrual undergarment 20 comprises a knit fabric. A particularly preferred knitting means involves first knitting a seamless tubular blank approximately half the final width of the menstrual undergarment 20. The tubular blank may be knit to have an hour glass shape so as to provide for the leg openings 60 in the finished menstrual undergarment 20 or, alternatively, portions of the opened tube may be cut away to provide for such leg openings 60 (see Forming the Undergarment below).

The Elasticized Waistband

As noted above, the waist opening 21 allows entry into the undergarment 20 of the present invention. Preferably the waist opening 21 is provided with an elasticized waistband 22 such that the waist opening 21 conforms closely to a wearer's waist. The elasticized waistband 22 may be formed by providing an elastic member, such as a Lycra® or SPANDEX material, adjacent each distal end of the blank that is shown in FIG. 11, C-folding each distal end about itself to form end edges 23 and 24, and seaming the side edges 25–28 of the front panel 30 and the rear panel 40 to form the waist opening 21 and the elasticized waistband 22. Preferably, the elasticized waistband 22 comprises the same yarns as and is integrally knit with the front panel 30 and the rear panel 40. More preferably, the elasticized waistband 22 comprises a turned welt as is known to the art. A particularly preferred knitting pattern for the elasticized waistband 22 comprises a combination of plain knit stitches and float stitches wherein every fourth wale is provided with a positive float stitch.

The Front Region

As can be seen in FIGS. 1 and 2, the front region, as exemplified by front panel 30, is that portion of the menstrual undergarment 20 that co-operates with the rear panel 40 (discussed below) to encircle a wearer's waist and hips. As can be also seen in FIGS. 1 and 2. the front panel 30, the rear panel 40, and the crotch panel 50 also co-operate to define the leg openings 60 (discussed in detail below). The front panel 30 is also preferably extensible in at least the longitudinal direction, preferably both the longitudinal and transverse directions, so that it is able to readily conform to a wide range of bodily shapes.

While alternate structures can be used, for example, the front panel 30 could be cut to an appropriate shape from a woven or nonwoven material and joined to the remaining portions of the menstrual undergarment 20. the front panel 30 of the present invention is preferably wholly plain knit, more preferably jersey knit, from a combination of elastically extensible and non-elastically extensible yarns. As is clear to one of ordinary skill in the art, the elastic properties of the individual yarns and the particular knitting pattern can be used by a designer to define the mechanical properties of the front panel 30. In a particularly preferred embodiment of the present invention. the front panel 30 comprises alternating courses of wholly plain knit, preferably jersey knit, nylon and Lycra® or SPANDEX yarns as are available from Unifi, Inc. of Greensboro, N.C. In an alternative embodiment, the front panel 30 can be wholly plain knit, preferably jersey knit, using a Lycra® or SPANDEX yarn having suitable mechanical properties in all courses. As will be clear from the discussion of the mechanical properties of the front panel 30 below, one of skill in the art could define other knitting patterns using alternative yarns to provide such mechanical properties. As noted above, front panels 30 comprising woven or nonwoven materials having such mechanical properties as are described below are also envisioned.

In the preferred embodiment of the present invention shown in FIGS. 1, 2, and 11, the front panel 30 is extensible in at least the longitudinal direction. Preferably, the front panel 30 is elastically extensible in both the longitudinal and transverse directions. Such elastic extensibility enables the menstrual undergarment 20 of the present invention to fit a variety of bodily shapes and sizes and provides good conformity to a wearer's body. An extensible front panel 30 further co-operates with the rear panel 40 and the crotch panel 50 to provide a "z-direction" biasing force to the crotch panel 50 throughout a wide range of wearer movements. Such a biasing force helps maintain a catamenial device 200 (FIG. 12) as may be worn with the menstrual undergarment 20 in close bodily contact, particularly with a wearer's pudendal region. More preferably, the biasing force directs an absorbent article, such as catamenial device 200. such that the article is held closely against a wearer's body, wherein the front edge 202 of such a device lies in a position slightly anterior to the introitus and the rear edge 204 thereof lies posterior to the perineum. Still more preferably, such a biasing force maintains the device 200 in such a position throughout a wide range of wearer motions. This biasing force will be discussed below in greater detail in the Longitudinal Stretch Control Member section below. Preferably, the front panel 30 is constructed so as to have a longitudinal stretch modulus of between about 1 gram/inch (0.4 grams/centimeter) and about 50.0 grams/inch (19.7 grams/centimeter). More preferably the longitudinal stretch modulus is between about 3 grams/inch (1.2 grams/centimeter) and about 40 grams/inch (15.7 grams/centimeter). Particularly preferably, the longitudinal stretch modulus of the material comprising the front panel 30 is quite low (particularly in comparison to other undergarments of the art) and lies between about 3 grams/inch (1.2 grams/centimeter) and about 20 grams/inch (7.9 grams/centimeter). A suitable method for measuring stretch modulus is described in the TEST METHODS section below.

The Rear Region

As noted above, the rear region, as exemplified by rear panel 40, cooperates with the front panel 30 to encircle a wearer's waist and hips. As is shown most clearly in FIG. 11, the rear panel 40 comprises first and second sections 44, 46. The sections 44, 46, which are separated by the longitudinally extending, extensible lifting member 42 (discussed as a separate element below), provide coverage to a wearer's buttocks and have disposed thereon a portion of the elasticized waistband 22 which encircles a wearer's waist. The rear panel 40 is also preferably elastically extensible in at least the longitudinal direction, preferably both the longitudinal and transverse directions, so that it is able to readily conform to a wide range of bodily shapes.

In a manner similar to the front panel 30. the first and second sections 44, 46 of the rear panel 40 are preferably wholly plain knit, more preferably jersey knit, from a combination of elastically extensible and non-elastically extensible yarns. Again, other materials, such as the cut and sewn woven or nonwoven materials discussed above, which also have the requisite mechanical properties, are also suitable. As is clear to one of ordinary skill in the art, the elastic properties of the individual yarns and the particular knitting pattern can be used by a designer to define suitable mechanical properties. In a particularly preferred embodiment of the present invention, the first and second sections 44. 46 of the rear panel 40 comprise alternating courses of wholly plain knit, preferably jersey knit, nylon and Lycra® or SPANDEX yarns as are available from Unifi, Inc. of Greensboro, N.C. In an alternative embodiment, the front panel 30 can be wholly plain knit, preferably jersey knit. using a Lycra® or SPANDEX yarn having suitable mechanical properties in all courses. As will be clear from the discussion of the mechanical properties of the first and second sections 44, 46 of the rear panel 40 below, one of skill in the art could define other knitting patterns using alternative yarns to provide such mechanical properties.

In the preferred embodiment of the present invention shown in FIGS. 1, 2, and 11, the first and second sections 44, 46 of the rear panel 40 are extensible in at least the longitudinal direction. Preferably, the sections 44, 46 are elastically extensible in both the longitudinal and transverse directions. Such elastic extensibility enables the menstrual undergarment 20 of the present invention to fit a variety of bodily shapes and sizes and provides good conformity to a wearer's body. An extensible rear panel 40 further co-operates with the front panel 30, the lifting member 42, and the crotch panel 50 to provide a "z-direction" biasing force to the crotch panel 50 throughout a wide range of wearer movement. Such a biasing force helps maintain a catamenial device 200 (FIG. 12) as may be worn with the menstrual undergarment 20 in close bodily contact, particularly with a wearer's pudendal region. More preferably, such a biasing force directs the catamenial device 200 to a relationship with a wearer's body wherein the front edge 202 of such a device lies in a position slightly anterior to the introitus and the rear edge 204 thereof lies posterior to the perineum. Still more preferably, such a biasing force maintains the device 200 in such a position throughout a wide range of wearer motions. This biasing force will be discussed below in greater detail in the Longitudinal Stretch Control Member section below. Preferably, the rear panel 40 is constructed so as to have a longitudinal stretch modulus of between about 1 gram inch (0.4 grams/centimeter) and about 50.0 grams/inch (19.7 grams/centimeter). More preferably the longitudinal stretch modulus is between about 3 grams/inch (1.2 grams/centimeter) and about 40 grams/inch (15.7 grams/centimeter). Particularly preferably, the longitudinal stretch modulus of the material comprising the first and second sections 44, 46 of the rear panel 40 is quite low (particularly in comparison to other undergarments of the art) and lies between about 3 grams/inch (1.2 grams/centimeter) and about 20 grams/inch (7.9 grams/centimeter). A suitable method for measuring stretch modulus is described in the TEST METHODS section below.

The Lifting Member

The lifting member 42 co operates with the rear panel 40 to provide a "z-direction" biasing force along the longitudinal centerline L of the menstrual undergarment 20 of the present invention. This force helps lift the crotch panel 50, particularly the longitudinal stretch control 52 member that is disposed therein, so that the crotch panel 50 and any catamenial device 200 that may be disposed thereon is in close body contact. In particular, without being bound by theory, the lifting member 42 is believed to direct the elastic forces provided by the rear panel 40 along the longitudinal centerline L to help lift the crotch panel 50 into close bodily contact.

As noted above, the lifting member 42 helps provide a "z-direction" biasing force along the longitudinal centerline L. Therefore, the lifting member 42 is preferably disposed along the longitudinal centerline L in the rear panel 40. More preferably, the lifting member 42 divides the rear panel 40 into symmetric first and second sections 44, 46. The lifting member 42 can be joined to the rear panel 40 along the longitudinal centerline L. Preferably, the lifting member 42 is integral to the rear panel 40. In the particularly preferred embodiment shown in FIGS. 1, 2, and 11, the lifting member 42 is integrally knit with the first and second sections 44, 46 of the rear panel 40.

To facilitate the direction of forces, the lifting member 42 should have less stretch than the first and second sections 44, 46 of the rear panel 40. To provide such lower stretch, the lifting member 42 may comprise a material having a higher stretch modulus than the rear panel 40 or a knit material having a knit pattern as is known in the art to provide greater stretch resistance. Higher stretch modulus materials suitable for use as a lifting member 42 include high modulus film materials, such as a polyester film material or even a single strand of yam or monofilament having a relatively high modulus (e.g. cotton, polyester or nylon). Preferably, the lifting member 42 comprises the same yams as are suitable for the first and second sections 44, 46 of the rear panel 40 and is integrally knit therewith using a knit pattern having less stretch than the first and second sections 44, 46. That is, the yams discussed above with respect to the first and second sections 44, 46 of the rear panel 40 are also suitable for the lifting member 42. A particularly preferred knitting pattern for the lifting member 42 uses stitches known in the art to provide reduced stretch.

For example, a pattern of tuck stitches, float stitches, or a combination of tuck and float stitches has been found to be suitable.

As noted above, the Applicants believe that the lifting member 42 helps direct lifting forces provided by the rear panel 40 along the longitudinal centerline L because the lifting member 42 has a higher stretch modulus than the rear panel 40. In particular, the lifting member 42 preferably has a longitudinal stretch modulus of between about 50 grams/inch (19.7 grams/centimeter) and about 110.0 grams/inch (43.3 grams/centimeter). More preferably, the longitudinal stretch modulus is between about 60 grams/inch (23.6 grams/centimeter) and about 100 grams/inch (39.4 grams/centimeter). A suitable method for measuring stretch modulus is described in the TEST METHODS section below.

In an alternative embodiment of the lifting member (not shown) the lifting member comprises two opposed portions each of which extends upwardly and laterally outwardly at an acute angle to the longitudinal centerline on opposite sides thereof. The portions meet in an area of juncture at the rear end of the longitudinal stretch control member. Preferably, the portions comprising this alternative embodiment mirror each other on opposite sides of the longitudinal centerline. One of skill in the art will recognize that such a structure divides the rear panel 40 into three portions.

By extending upward and outward at an acute angle from the rear end of the longitudinal stretch control member 52 the portions of this alternative embodiment direct those forces resulting from extension of the rear panel 40 such that they converge on the rear end of the longitudinal stretch control member providing a "z direction" biasing force thereto. Preferably, the acute angle is between about 15 degrees and about 45 degrees. More preferably, the acute angle is about 35 degrees.

The Crotch Region

The crotch region, as exemplified by crotch panel 50, is positioned along the longitudinal centerline L of the menstrual undergarment 20 of the present invention between the front panel 30 and the rear panel 40. In the preferred embodiment of the present invention shown in FIG. 11, the crotch panel 50 comprises several portions that are divided by the longitudinal stretch control member 52 and the angled stretch control members 54. In the preferred embodiment of the present invention shown in FIGS. 1, 2, and 11, the crotch panel 50 co operates with the front panel 30 and the rear panel 40 to define the leg openings 60. The crotch panel 50 is that portion of the menstrual undergarment 20 that has most direct contact with a wearer's pudendal area. The crotch panel 50 also supports any catamenial device 200 that may be worn with such an undergarment 20.

The crotch panel 50 of the present invention is particularly able to conform to a wearer's pudendal region. Without being bound by theory, it is believed that the conformity of the crotch panel 50 of the present invention is due to the low lateral stretch modulus of the materials used therefor. In particular, as noted above, the lifting member 42 cooperates with the rear panel 40 to provide a "z direction" biasing force along the longitudinal centerline of the undergarment 20 (i.e. along the longitudinal stretch control member 52). The Applicants believe there is a similar "z directed" component to the force provided by the leg elastics 62 that causes the leg elastics to be lifted into the crease between a wearer's pudendal area and her legs. As is shown most clearly in FIG. 11, the crotch panel 50 bridges the distance between the longitudinal stretch control member 52 and the leg elastics 62 (i.e. the distal edge 56 of the crotch panel is adjacent to the leg elastics). Because the crotch panel 50 has a low lateral stretch modulus and because it is provided with a "z direction" force at two laterally spaced apart locations, the Applicants believe that the crotch panel 50 is lifted by the longitudinal stretch control member and the leg elastics and stretched thereby so as to readily conform to external surfaces of those portions of a wearer's pudendal area which lie between the labial cleft and the leg crease.

Figure 10:
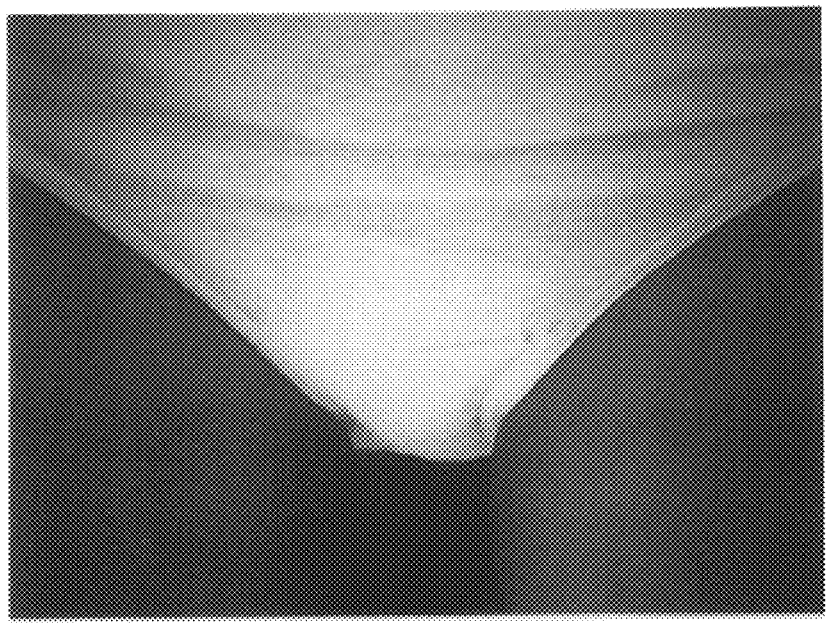
FIG. 10 is a frontal photograph of a conventional knit undergarment of the prior art with the wearer's legs open.

This conformity is maintained over a wide range of movement. The conformity is shown particularly clearly in FIGS. 7 and 8 from Example 1 which photographically show that the close body contact of the crotch panel 50 of the present invention is maintained when a wearer's legs are close together and when they are spread apart. In contrast. the conventional prior art undergarment, as is shown in FIGS. 9 and 10. sags below the wearer's pudendal area (i.e. there is no close contact between the crotch of the prior art undergarment and the wearer's pudendal area).

As noted above, it is important that the lateral stretch modulus of the crotch panel 50 be low so as to enable conformity thereof to a wearer's pudendal area. Crotch panels 50 having a lateral stretch modulus of between about 1 gram/ inch (0.4 grams/centimeter) and about 50 grams/ inch (19.7 grams/centimeter) have been found to be suitable for the present invention. Preferably, the crotch panel 50 has a lateral stretch modulus of between about 5 grams/ inch (2.0 grams/centimeter) and about 40 grams/ inch (15.7 grams/ centimeter), more preferably between about 10 grams/ inch (3.9 grams/centimeter) and about 30 grams/ inch (11.8 grams/centimeter).

The crotch panel 50 can comprise any woven material, nonwoven material, knit material, or the like that possesses the requisite physical properties as described below. Preferably the crotch panel 50 comprises a knit material having a higher longitudinal stretch modulus than the front panel 30, the rear panel 40 or the lifting member 42. More preferably, as is shown in FIGS. 1, 2, and 11, the crotch panel 50 is integrally knit with the front panel 30 and the rear panel 40 using a plain knit pattern and yarns having a low extensibility to provide stretch resistance. Additional stretch resistance is provided by the longitudinal stretch control member 52 and the angled stretch control members 54 which are discussed below. The crotch panel 50 also has a lower stretch resistance than the gusset areas of stiff undergarments of the prior art that fail to conform to a wearer's pudendal area.

Suitable yarns for the crotch panel 50 have a relatively high stretch modulus (i.e. yarns that would not be considered elastically extensible by the art). Suitable yarns include natural yarns, such as cotton yarns and wool yams. and synthetic yarns, such as nylon yams, polyester yarns, acrylic yams, and other synthetic yams having the requisite mechanical properties. Particularly preferred yarns include nylon yarns and cotton yarns.

Alternatively, if an elastically extensible crotch panel 50 is desired, Lycra® or SPANDEX yarns having a greater stretch modulus than the similar Lycra® or SPANDEX yams used for the front panel 30 and the rear panel 40 can be used.

Longitudinal Stretch Control Member

As noted above the longitudinal stretch control member 52 serves to limit the stretch of the crotch panel 50. In particular, the longitudinal stretch control member 52 limits the longitudinally oriented stretch of the crotch panel 50. Preferably, the longitudinal stretch control member 52 has a greater resistance to stretching than the front panel 30, the rear panel 40 or the lifting member 42 and less resistance to stretching than undergarments of the prior art that fail to conform to a wearer's pudendal area. Consequently, the longitudinal stretch control member 52 has a higher longitudinal stretch modulus than either of the aforementioned front or rear panels and a lower stretch resistance than certain stiff gussets of the prior art. In particular, the longitudinal stretch control member 52 has a longitudinal stretch modulus of between about 50 grams/ inch (19.7 grams/ centimeter) and about 500 grams/ inch (196.8 grams/ centimeter). Such modulus being measured using samples taken along the longitudinal centerline L of the undergarment 20 (i.e. a portion of the crotch panel 50 may also contribute to the measured modulus). More preferably, the stretch modulus is between about 50 grams/ inch (19.7 grams/centimeter) and about 300 grams/ inch (118.1 grams/ centimeter). Particularly preferred crotch panels 50 of the present invention have a longitudinal stretch modulus, as measured along the longitudinal centerline thereof, of between about 100 grams/ inch (39.4 grams/centimeter) and about 200 grams/ inch (78.7 grams/centimeter).

While not being bound by theory, such longitudinal stretch limitation is believed to transfer forces from the rear panel 40 (particularly the lifting member 42 therein) and from the front panel 30 to the crotch panel 50 to provide a "z-direction" biasing force thereto. Such force transfer causes the crotch panel 50 and any catamenial device 200 disposed thereon to be held closely against a wearer's pudendal area (particularly along the longitudinal centerline L of the menstrual undergarment 20) throughout a wide range of wearer movements. More precisely, the crotch panel 50 and catamenial devices 200 disposed thereon have been found to be at least partially disposed between the distal ends of a wearer's labia when a menstrual undergarment 20 of the present invention is worn.

It is particularly important to note that the "z-direction" biasing force is higher along the longitudinal centerline L (FIG. 11) of the undergarment 20 of the present invention. That is, the first body contact force, as is provided by the longitudinal stretch control member 42. is greater than the forces provided by other portions of the crotch panel 50 that lie laterally outboard of the longitudinal stretch control member 42. Such increased force is believed to be particularly effective in lifting any absorbent article that may be disposed on the crotch panel 50 into a close relationship with a wearer's vaginal introitus and urethra so as to allow ready interception of bodily fluids that may be exuded therefrom.

While it is important that the "z-direction" biasing force is higher along the longitudinal centerline, there should be an upwardly directed second body contact force over substantially the entire external surface of a wearer's labia. Such lower second body contact force causes any absorbent article disposed on the crotch panel 50 to also conform to the labial surface which provides a "seal" against the distal edges of a wearer's labia majora further reducing the risk of bodily fluids flowing along the surface of the absorbent article to an edge thereof with resulting leakage. On the other hand, a loose prior art garment, such as that shown in FIGS. 3, 4, 9, and 10, provides no such seal.

Body contact forces, such as the "z-direction" biasing force discussed above and the forces causing the garment of the present invention to contact the external surface of a wearer's labia may be estimated using the body contact force test method described in the panel 50 to assume the "modified" cusp configuration shown in FIGS. 5–8. Such a configuration allows both interception of bodily fluids close to the point of exit from the body and the additional leakage protection of a "seal" against a wearer's labia. In order to achieve this "modified" cusp configuration, the ratio of body contact force along the centerline to the body contact force at the distal edge of the labia majora should be greater than 1:1 when such forces are measured according to the method given in the TEST METHODS section. Preferably the ratio of centerline force to distal edge force is greater than about 1.25:1, more preferably, the ratio is greater than about 1.5:1.

Obviously the actual force values are also important. If the force is too low, the garment will not maintain an absorbent article in close body contact throughout a wide range of wearer motions. If the force is too high, discomfort can result. Suitably, the force along the longitudinal centerline is greater than about 2 g/cm$^2$. Preferably the first body contact force (i.e. along the longitudinal centerline) is greater than about 2.1 g/cm$^2$, more preferably greater than about 2.2 g/cm$^2$. Suitably, the force is less than about 20 g/cm$^2$, preferably less than about 15 g/cm$^2$. more preferably, less than about 10 g/cm$^2$. Similarly, the second force as measured at the apex of the labia majora is suitably greater than about 1 g/cm$^2$, preferably greater than about 1.1 g/cm$^2$, more preferably greater than about 1.2 g/cm$^2$ and less than about 20 g/cm$^2$, preferably less than about 15 g,/cm$^2$, more preferably less than about 10 g/cm$^2$.

This force transfer and the resulting close body contact can be further demonstrated by comparing Lift according to the method described in the Test Methods section below (This method is a modification of the method described in U.S. Patent application Serial No. 08/383,536, filed in the name of Osborn III, et al. on Feb. 1, 1995, the disclosure of which is incorporated herein by reference) for the menstrual undergarment 20 of the present invention and for undergarments of the prior art. Such measurements are reported in Table 1 below.

TABLE 1

Comparative Lift Measurements

| Undergarment Tested | Lift in Millimeters (391 grams applied force) | | |
|---|---|---|---|
| | Position 1 | Position 2 | Position 3 |
| Present Invention | 21 | 30 | 38 |
| WonderBody ™[1] | 14 | 23.5 | 33.5 |
| Olga Secret Shapers ®[2] | 9 | 19.5 | 29 |
| Japanese Menstrual Shorts[3] | 10.5 | 15.5 | 25 |
| Hanes Her Way[4] | 4 | 8.5 | 23 |

TABLE 1-continued

Comparative Lift Measurements

| Undergarment Tested | Lift in Millimeters (391 grams applied force) | | |
|---|---|---|---|
| | Position 1 | Position 2 | Position 3 |

[1]Available from Sara Lee Intimates, Winston-Salem, NC
[2]Available from Olga Company, Van Nuys, CA
[3]Available from UniCharm of Japan as Sofy Sports
[4]Available from Sara Lee Intimates, Winston-Salem, NC As can be clearly seen in Table 1, the menstrual undergarment 20 of the present invention has greater Lift (closer body contact) at all positions of the test apparatus. The difference is most dramatic at Position 1, which, as is described in the aforementioned Osborn, III application, is intended to correspond to the labial area of a wearer's body. Because of the aforementioned higher force along the centerline L, the garment 20 of the present invention is able to provide this improved lift and the resulting closer body contact. The menstrual undergarment 20 of the present invention preferably has a Lift at Position 1 in the Lift Test apparatus of greater than about 16 mm, a Lift at Position 2 of greater than about 25 mm, and a Lift in Position 3 greater than about 35 mm. More preferably the Lift in Position 1 is greater than about 18 mm, the lift in Position 2 is greater than about 27 millimeters, and the Lift in Position 3 is greater than about 36 mm.

The undergarment 20 of the present invention is particularly comfortable to wear (particularly in the pudendal area), notwithstanding the close conformity of the present undergarment to and contact with a wearer's body. Undergarments of the prior have attempted to achieve conformity to the pudendal area by elasticized lifting members, such as cinches, or by a very tight fit overall, such as is seen with Japanese menstrual shorts. Undergarments of either type are often described as uncomfortable. One source of such discomfort, particularly for cinch-type undergarments, is pressure on a wearer's anus. The tissue surrounding the anus is particularly sensitive to pressure and forces applied to the anus can cause discomfort. Cinch-type undergarments, such as that described in the aforementioned U.S. Pat. No. 3,608,551, typically use an elastically extensible member to provide a lifting force to seal an absorbent article against a wearer's perineum. Such elastic members are usually joined to the undergarment at a location that is positioned above a wearer's anus when the undergarment is worn. As a result, there is not only the desirable lifting force to seal an absorbent article against the wearer's perineum but also an uncomfortable pressure on a wearer's anus. On the other hand, the undergarment 20 of the present invention distributes the "z-direction" biasing force discussed above so that bodily contact is maintained throughout a wide range of wearer motions without unacceptable pressure on a wearer's anus. Without being bound by theory, it is believed that the forces distributed along the longitudinal centerline L of the present undergarment 20 are isolated at a point posterior to the anus and on the perineum so that the anus is at least partially bridged by the longitudinal stretch control member 52 with a resulting reduction in force on the anus.

As shown most clearly in FIG. 11, the longitudinal stretch control member 52 is disposed along the longitudinal centerline L in the crotch panel 50. The longitudinal stretch control member 52 can be either a separate element joined to the crotch panel 50 or it can be integral to the crotch panel 50. Preferably, the longitudinal stretch control member 52 is integral to the crotch panel 50. In a particularly preferred embodiment of the present invention, the longitudinal stretch control member 52 and the crotch panel 50 are integrally knit.

As noted above, the longitudinal stretch control member 52 serves to limit stretch, particularly longitudinally oriented stretch in the crotch panel 50. To this end, the stretch control member can comprise any material having a greater stretch modulus than the crotch panel 50. For example, the stretch control member could comprise a high modulus film material or even a single strand of yarn or monofilament having a relatively high modulus.

For the preferred integrally knit longitudinal stretch control member 52 discussed above, the longitudinal stretch control member could comprise the same yarns used for the crotch panel wherein the yarns comprising the stretch control member 52 were knit in a pattern known to the art as being stretch limiting. For example, the longitudinal stretch control member 52 can comprise a knit pattern wherein alternating courses thereof are tucked. Alternatively, an elastic yarn can be floated in to provide the longitudinal stretch control member 52 with additional stretch resistance as is also known in the art.

Suitable yarns for the longitudinal stretch control member 52 are substantially the same yarns or combinations of yarns as have been found to be suitable for the crotch panel 50.

Angled Stretch Control Members

Figure 12:
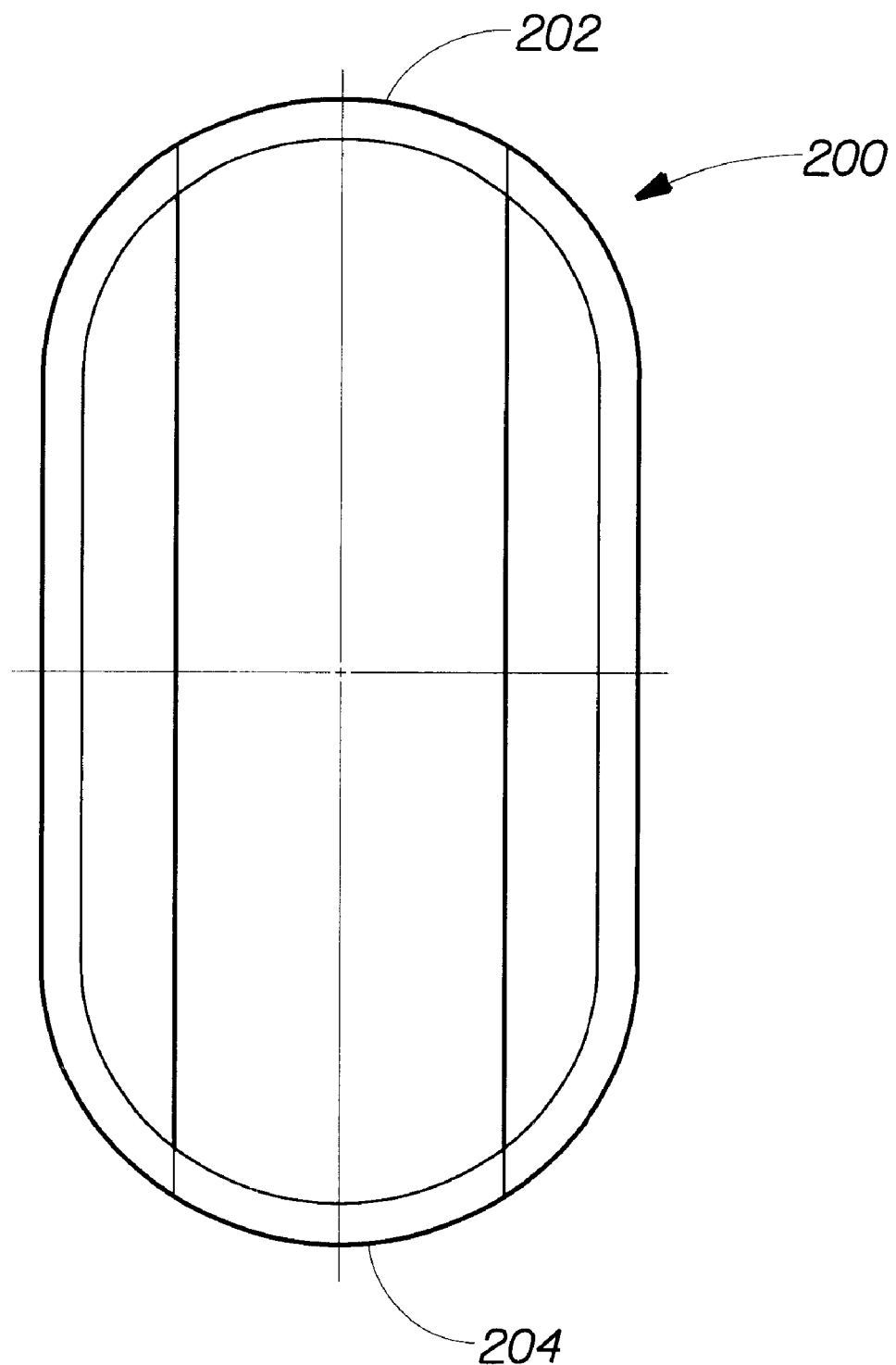
FIG. 12 is a plan view of an absorbent article suitable for use with the present invention.

The angled stretch control members 54 also serve to control the stretch of the crotch panel 50. In particular, the angled stretch control members 54 provide a vector that limits laterally oriented stretch in the crotch panel 50. Because there is also a longitudinally oriented stretch control vector provided by the angled stretch control members 54. the angled stretch control members 54 also cause the crotch panel 50 and any catamenial device 200 disposed thereon to curve upward and around the external surfaces of a wearer's labia. Without being bound by theory, the angled stretch control members 54 are believed to help transfer the forces provided by the leg elastics 62. the front panel 30 and the rear panel 40 to the crotch panel 50 resulting in this curved, cup-like configuration. This force transfer also appears to provide a resistive force that minimizes narrowing of the crotch panel 50 on longitudinal extension of the menstrual undergarment 20 (i.e. Poisson narrowing is minimized). This minimization is believed to help reduce motion of the crotch panel 50 relative to a wearer's body as the wearer moves. In other words, it is best understood that the angled stretch control members 54 help make the crotch panel 50 a "low motion zone" with a resulting reduction in the relative motion between a wearer's body and the crotch panel 50. As a result any absorbent article that may be disposed on the crotch panel 50 (e.g. a catamenial device 200 as shown in FIG. 12) is more likely to remain in a constant relation with the wearer's pudendal region.

As shown most clearly in FIG. 11, the angled stretch control members 54 are disposed at an angle A relative to the longitudinal centerline L in the crotch panel 50. The angled stretch control members 54 can be either a separate element joined to the crotch panel 50 or they can be integral to the crotch panel 50. Preferably, the angled stretch control members 54 are integral to the crotch panel 50. In a particularly preferred embodiment of the present invention, the angled stretch control members 54 and the crotch panel 50 are integrally knit.

Angle A is believed to help control the degree of upward curvature provided by the force transfer discussed above. If the angle A is too small, there is insufficient transfer of force from the leg elastics 62 so the crotch panel incompletely wraps the sides of a wearer's labia. If the angle A is too large, there is insufficient transfer of force from the front panel 30 and the rear panel 40 so there is reduced contact at the mons and the perineum. Preferably the angle A is between about 30 degrees and about 75 degrees. More preferably, the angle A is between about 45 degrees and about 75 degrees. In a particularly preferred embodiment of the present invention, the angle A is about 60 degrees.

As can also be seen most clearly in FIG. 11, the angled stretch control members 54 are preferably longitudinally symmetric. That is, the angled stretch control members 54 are preferably provided in opposed pairs wherein one of each pair extends laterally outwardly at an angle A from the longitudinal stretch control member 52 toward the leg elastics 62. Although other embodiments having differing numbers of such pairs are contemplated, the preferred embodiment of the present invention comprises two pairs of angled stretch control members 54 with one pair on each side of the transverse centerline T. A plurality of angled stretch control members 54 is believed to be desirable because such a plurality provides an even distribution of forces such that the crotch panel 50 smoothly wraps the external surfaces of a wearer's labia when a menstrual undergarment 20 of the present invention is worn.

Other embodiments of the present invention having differing orientations and positions for the angled stretch control members 54 are also contemplated. For example, while the angled stretch control members 54 are shown in FIG. 11 as extending forwardly outward (i.e. toward the front panel 30), the angled stretch control members 54 may also extend rearwardly outward (i.e. toward the rear panel 40). The angle A for such embodiments is still an acute angle and has the same ranges as described above. Further, embodiments wherein a portion of the plurality of angled stretch control members 52 extends forwardly outward and a portion of such members extends rearwardly outward are also contemplated. In one example, not shown but similar to the undergarment 20 shown in FIG. 11, there are no angled stretch control members 54 positioned in the front portion of the undergarment 20 (i.e. the portion on the side of the transverse centerline T that also contains the front panel 30) but two rearwardly directed angled stretch control members 54 are positioned in the rear portion of the undergarment 20. When evaluated for bodily fit, this embodiment of the present invention performed comparably to undergarment 20 described above.

In a manner similar to the longitudinal stretch control member 52. the angled stretch control members 54 serve to limit stretch in the crotch panel 50. In particular, the angled stretch control members serve to limit lateral stretch. Preferably, an angled stretch control 54 has a lateral stretch modulus of between about 50 grams/inch (19.7 grams/centimeter) and about 500 grams/inch (196.8 grams/centimeter). More preferably, the stretch modulus is between about 50 grams/inch (19.7 grams/centimeter) and about 300 grams/inch (118.1 grams/centimeter). Particularly preferred crotch panels 50 for use in the present invention have angled stretch control members 54 with a stretch modulus of between about 100 grams/inch (39.4 grams/centimeter) and about 200 grams/inch (78.7 grams/centimeter).

The angled stretch control members 54 can comprise substantially the same materials as are suitable for the longitudinal stretch control member 52 since both elements tend to limit the stretch of the crotch panel 50. For the preferred integrally knit angled stretch control members 54 discussed above, the angled stretch control members 54 could comprise the same yarns used for the crotch panel wherein the yarns comprising the angled stretch control members 54 are knit in a pattern known to the art as being stretch limiting. For example, the angled stretch control members 54 can comprise a knit pattern wherein alternating courses thereof are tucked. Alternatively, a pattern of float stitches can be used to provide the angled stretch control members 54 with additional stretch resistance as is also known in the art.

Suitable yarns for the angled stretch control members 54 are substantially the same yarns as have been found to be suitable for the crotch panel 50.

Elasticized Leg Openings

As can be seen in FIGS. 1, 2. and 11, the menstrual undergarment 20 of the present invention is also provided with a pair of elasticized leg openings 60. As noted above, the front panel 30, the rear panel 40, and the crotch panel 50 cooperate to define the periphery of each leg opening 60. This periphery is provided with a leg elastic 62 for elasticization of the opening 60. The leg elastics 62 cooperate with the front panel 30, the rear panel 40, and the crotch panel 50 to provide a "z-direction" biasing force to the crotch panel 50 throughout the full range of wearer movement. In particular, the leg elastics provide the distal edge 56 of the crotch panel 50 (i.e. the edge of the crotch panel 50 that helps define the leg opening 60) with a "z-direction" biasing force that lifts the edge 56 causing the crotch panel 50 to conform to the exterior surfaces of a wearer's labia. Said another way, and shown most clearly in FIGS. 1 and 2, the nature of the leg cut opening 60 also is preferably designed to direct the contractive force of the leg elastics 62 in a more vertical direction than would be possible if a more circular shape would be used for the leg opening 60

That is, the front panel 30, the rear panel 40, the crotch panel 50, and the leg elastics 62 cooperate to provide a catamenial device 200 that may be disposed on the crotch panel 50 with a uniform upward force against a wearer's body such that the catamenial device is held closely against a wearer's pudendal area throughout a wide range of wearer motions. The leg elastics 62 also preferably cooperate with the angled stretch control members 54 to provide a force vector that causes the crotch panel 50 and any catamenial device 200 that may be disposed thereon to wrap around the external surfaces of a wearer's labia.

While the leg elastics 62 must provide a minimal contractive force around the periphery of the leg opening 60 for proper fit of the undergarment 20, it is important that the contractive force not be so great as to cause discomfort to a wearer. The Applicants have found that a contractive force of at least about 20 grams is necessary to minimize the risk of gapping around the periphery of the leg opening 34. Preferably the contractive force should be at least about 40 grams. More preferably, the contractive force should be at least about 80 grams. Minimizing the stretch modulus over the range of expected elastic extensions during the wear cycle also minimizes the risk of wearer discomfort. That is, if the leg elastics are designed to provide a contractive force of about 80 grams at a typical in use extension, that force should not substantially increase for greater extensions that may either be due to a different wearer leg circumference or due to wearer movement. The Applicants have found that a stretch modulus for the leg elastics between about 540 grams/inch (213 grams/centimeter) and about 590 grams/inch (232 grams/centimeter) provides a good balance between maintaining proper fit and minimizing wearer discomfort. Preferably, the stretch modulus of the leg elastics is between about 550 grams/inch (216 grams/centimeter) and about 580 grams/inch (228 grams/centimeter). Methods for measuring elastic contractions and stretch modulus is given in the TEST METHODS section below.

When such leg elastic materials are used as the leg elastics 62 in the garment 20 of the present invention they provide a third body contact force of at least about 5 grams/cm$^2$ (A body contact force of less than this value has been reported as being too loose by wearers). Preferably the third body contact force is greater than about 7 grams/cm$^2$. Garments having a third body contact forces on the order of 30 grams/cm$^2$ have been found to cause a high level of reported discomfort when worn. Therefore suitable garments 20 have a third body contact force less than this level. Preferably, the third body contact force is less than about 20 grams/cm$^2$. A particularly preferred garment 20 has a third body contact force between about 5 grams/cm$^2$ and about 10 grams/cm$^2$. This third body contact force is measured using a method similar to that described in the TEST METHODS section below. The main difference being that such testing is done by placing a cylinder having a circumference of 60 centimeters in the leg opening 60 to extend the leg elastics 62 rather than on a mannequin. The pressure sensor is placed between the leg elastic and the cylinder to measure the third body contact force.

The leg elastics 62 can be joined to the front panel 30, the rear panel 40, and the crotch panel 50 about the periphery of the leg opening 60 using means known to those of skill in the art. Specifically, the leg elastics 62 are joined to that portion of the side edges 25, 26, 27, 28 which will surround the leg openings 60 (i.e. form the periphery thereof).

For example, the leg elastics 62 can be joined to the shell portion 30 and the crotch panel 50 using adhesive means or by mechanical means, such as stitching. For the preferred knit menstrual undergarment 20 of the present invention, the leg elastics 62 are preferably joined to the front panel 30, the rear panel 40. and the crotch panel 50 by stitching thereto.

Optional Features

When used as a system with a catamenial device 200, the menstrual undergarment 20 of the present invention can also comprise a fastening system for reliably securing the catamenial device 200 on the crotch panel 50. For example, the catamenial device 200 could be provided with a first portion of a cohesive material and the crotch panel 50 could be provided with a second portion of a cohesive material. As used herein, a "cohesive material" is one which preferentially adheres to itself and not to other materials.

Alternatively, the garment-facing surface of a catamenial device 200 designed for use with the undergarment 20 of the present invention could comprise a skin-friendly mechanical fastening material comprising a substrate or surface with an array of prongs in the form of a plurality of small filamentous (or hair-like) projections disposed thereon as described in copending application Serial No. 60/065,294, filed on Nov. 13, 1998, in the names of Carstens, et al., the disclosure of which is incorporated herein by reference. Such projections are capable of easily adhering to knit material (e.g. the crotch panel 50 of the of the undergarment of the present invention), and have a sufficiently desirable holding force even if the supporting garment stretches and contracts.

Yet another alternative fastening material can comprise a material having a "T"-shaped or mushroom-shaped appearance when viewed from the side. One particularly preferred "T"-shaped mechanical fastening material for use on catamenial device 200 is a material known as TP200 available from 3M Personal Care and Related Products Division of Menomonie, Wis.

The crotch panel 50 can also optionally be provided with indicia (not shown) to help a wearer optimally position a catamenial device 200 therein. For example, such indicia can comprise markings on the leg elastics that would allow a wearer to properly locate any flaps that may be provided on a catamenial device 200 for use therewith. Alternatively, such indicia could comprise markings along the longitudinal centerline L that would allow a wearer to reliably position a catamenial device 200 each time a new device is disposed on the body contacting (i.e. inner) surface of the crotch panel 50.

The undergarment 20 of the present invention can also be used with a wide variety of catamenial devices and other types of absorbent articles. Exemplary devices are described in commonly assigned, copending patent application Serial No. 09/554,448, filed in the names of Carstens, et al. On the same date as the present application (Attorney's Docket Number Case 6923M), the disclosure of which is incorporated herein by reference. Such absorbent articles and the undergarment 20 of the present invention can also be used together to provide a highly efficient system comprising an absorbent article and the undergarment of the present invention. Such systems are described in commonly assigned, copending patent application Serial No. 09/554,483, filed in the names of Carstens, et al. on the same date as the present application (Attorney's Docket Number Case 7320), the disclosure of which is incorporated herein by reference.

Forming the Undergarment

A blank for the menstrual undergarment 20 is first knit in a tubular form using means known to the art. In particular, front panel 30, the rear panel 40, the crotch panel 50 are integrally knit. The rear panel 40 is provided with a lifting member 42 by having such a strip integrally knit therein. Similarly, the crotch panel 50 is provided with an integrally knit longitudinal stretch control member 52 and, preferably, a plurality of angled stretch control members 54. The appropriate knit patterns as described above are used.

The tubular blank is then slit walewise and opened. Excess material that would otherwise fill the leg openings 60 is removed to form a flat blank for the menstrual undergarment 20 having a shape similar to the plan view of the menstrual undergarment 20 that is shown in FIG. 11 As is further shown in FIG. 11, the blank for the menstrual undergarment has a front end edge 23, a rear end edge 24, front side edges 25, 26, and rear side edges 37A, 37B.

The leg elastics 62 are joined to the undergarment 20 about the periphery of the leg openings 60 as discussed above. The blank for the menstrual undergarment 20 is then folded about the transverse centerline T and opposing portions of the side edges that lie between the leg opening 60 and the end edges 23, 24 are joined (eg by sewing the edges) to form side seams 32, 34 completing the assembly of menstrual undergarment 20 (That is, the portion of side edge 25 that lies between the end of the leg elastic 62 in front panel 30 and the end edge 24 is joined to the portion of side edge 27 that lies between the end of the leg elastic 62 that lies in the rear panel 40 and the end edge 23 to form seam 32. Side edge 26 is joined to side edge 28 in a similar manner to form seam 34).

Alternatively, portions of the tubular knit blank can be cut out to provide the leg openings 60. For example, a tubular blank can be flattened, such that, the interior faces thereof contact each other and a pair longitudinally oriented side edges are formed. Leg opening precursors can then be formed by cutting matching portions having a semi-circular, semi-elliptical, or other desired shape from transversely opposite side edges at regular intervals along the flattened blank. Undergarment blanks are then formed by transversely cutting the flattened tubular blank in a predetermined repeat pattern wherein a first transverse cut is made across the material that was not removed when the leg opening precursors were formed to create a crotch portion precursor and a second transverse cut is made across the full width of the flattened tubular blank forming the waist opening 21. The leg elastics 62 are disposed about the periphery of each leg opening 60 and joined thereto. The two ends formed by the first transverse cut are joined by a single transverse seam to complete the crotch panel 50. The menstrual undergarment 20 is then finished by disposing the elasticized waistband 22 about the periphery of the waist opening 21 and joining the elasticized waistband 22 thereto.

The following examples serve to point out the particular benefits of various aspects of the present invention.

EXAMPLES

Example 1

This example is intended to demonstrate the "second skin" fit of the undergarment 20 of the present invention. Specifically. frontal photographs of the crotch region of the undergarment of the present invention and of a prior art knit undergarment were taken while a medical model wore each of the undergarments. The photographs were taken with the model standing with her legs in two positions: 1) a closed position (10 mm gap between the thighs) and 2) a spread position (50 mm gap between thighs). All photos were taken at a distance of 1 foot (30 centimeter) from the model's pudendal area.

Figure 7:
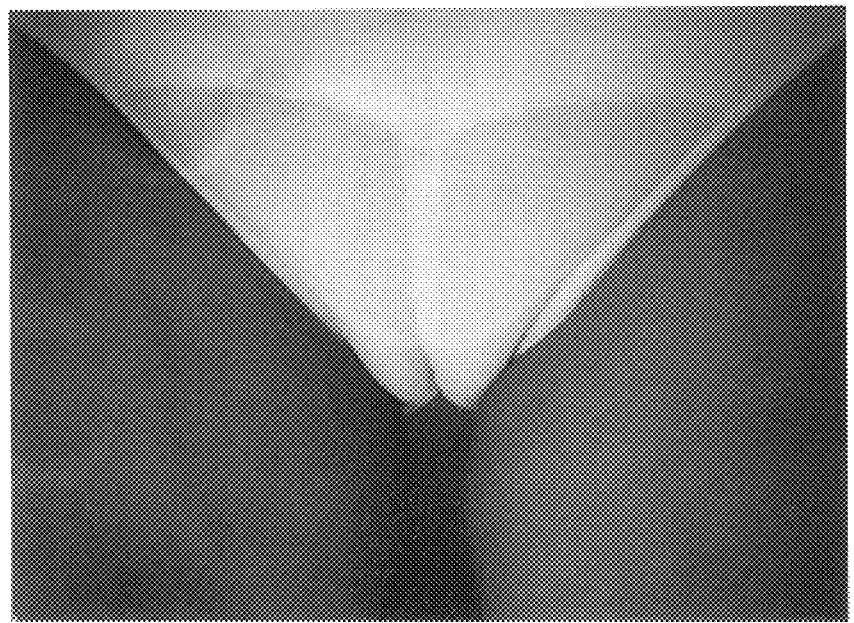
FIG. 7 is a frontal photograph of an undergarment of the present invention with the wearer's legs closed.
Figure 8:
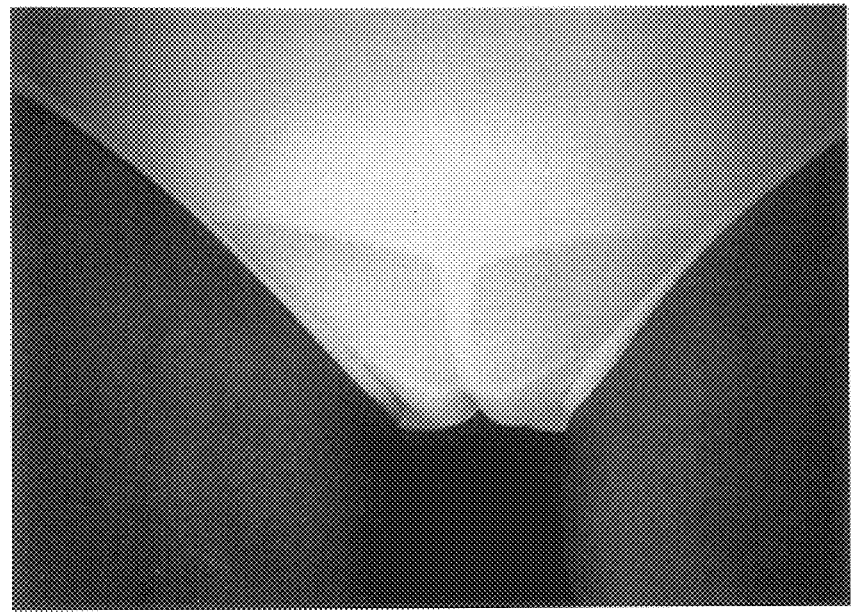
FIG. 8 is a frontal photograph of an undergarment of the present invention with the wearer's legs open.

FIGS. 7 and 8 show the undergarment of the present invention when the model's legs were in a closed and open position. FIGS. 9 and 10 show the same model in the same two positions wearing a knit undergarment of the prior art (Fruit of the Loom® available from Fruit of the Loom, Inc. of Bowling Green, Ky.). The results of this test are discussed in the Crotch Panel section above.

Example 2

This example is intended to show a comparison of body contact force among undergarments according to the present invention and several prior art undergarments.

Samples of the undergarment of the present invention and several prior art undergarments were evaluated for body contact force according to the method described in the TEST METHODS section. The results of this experiment are given in Table 2.

TABLE 2

Body Contact Force Comparison

| | | Body Contact Force | | |
| --- | --- | --- | --- | --- |
| Undergarment | Garmet Type | Centerline (grams/cm$^2$) | Labia Majora (grams/cm$^2$) | Force Ratio |
| Present Invention | N/A | 2.35 | 1.33 | 1.76 |
| Wing EC 8302[1] | A | 1.94 | 2.58 | 0.75 |

TABLE 2-continued

Body Contact Force Comparison

| Undergarment | Garmet Type | Centerline Body Contact Force (grams/cm²) | Labia Majora (grams/cm²) | Force Ratio |
|---|---|---|---|---|
| Wing EC 8400[1] | A | 1.10 | 1.57 | 0.70 |
| Fruit of the Loom[3] | B | 0.006 | 0.68 | 0.01 |
| Wacoal[2] | C | 0.50 | 2.52 | 0.20 |
| Wonder Body ™[4] | C | 0.07 | 0.77 | 0.09 |
| Olga 2903-28[5] | C | 0 | 0.50 | 0 |
| Olga 2903-18[5] | C | 0 | 0.29 | 0 |

[1] Available from Wacoal Corp. of Kyoto, Japan
[2] Available from Wacoal Corp. of Kyoto, Japan
[3] Available from Fruit of the Loom, Inc., Bowling Green, KY
[4] Available from Sara Lee Intimates, Winston-Salem, NC
[5] Available from Olga, Company, Van Nuys, CA
A Japanese Menstrual Short
B Unelasticized Panty
C Elasticized Panty The differences in the ratio of the body contact force along the centerline and the labial force among the products is clear.

TEST METHODS

Lift Test

Introduction

This test involves the use of a lift measuring test apparatus that is shaped to roughly approximate the various areas of a female body that the sample must fit adjacent in order to achieve close body contact. The lift measuring test apparatus comprises two curved PLEXIGLAS pieces that are intended to approximate the portions of the wearer's body that the crotch of the wearer's undergarments contact during wear. The apparatus contains a longitudinally-oriented slit-like opening that is intended to approximate the space between the wearer's labia and the crevice between the wearer's buttocks (the "gluteal groove"). The sample is attached to clamps which are adjusted to simulate the forces exerted when a woman's panties are pulled up to the wearer's body. The distance that the middle of the sample vertically intrudes into the slit-like opening is measured to provide a relative measurement of body contact.

Apparatus
Lift Measuring Apparatus

The lift measuring test apparatus comprises six pieces of PLEXIGLAS arranged as shown in FIGS. 13–18. The Lift Test apparatus 100 has an inside surface 110A, an outside surface 100B, a front portion 100C, and a rear portion 100D.

Figure 13:
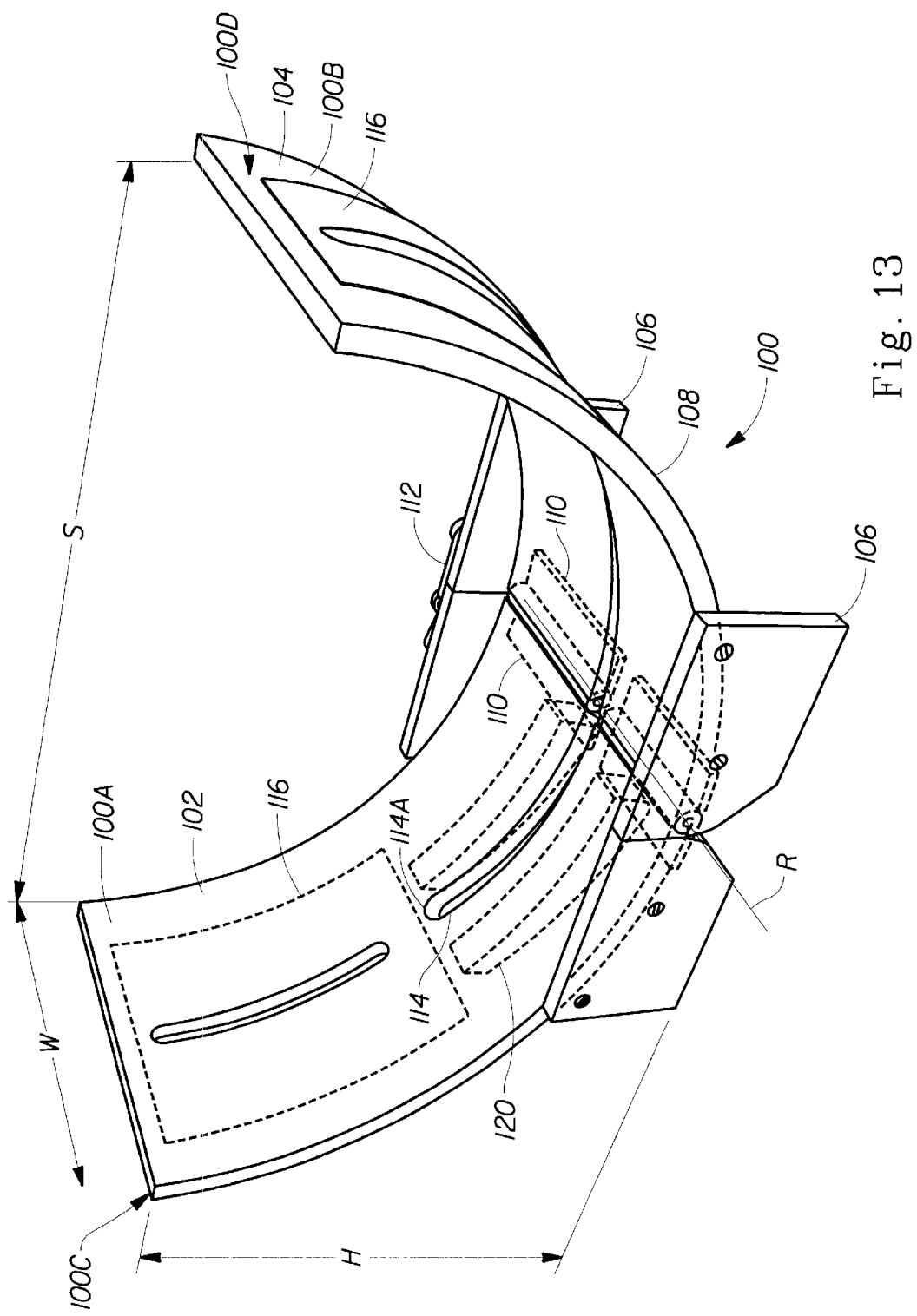
FIG. 13 is a perspective view of the Lift Test apparatus.
Figure 14:
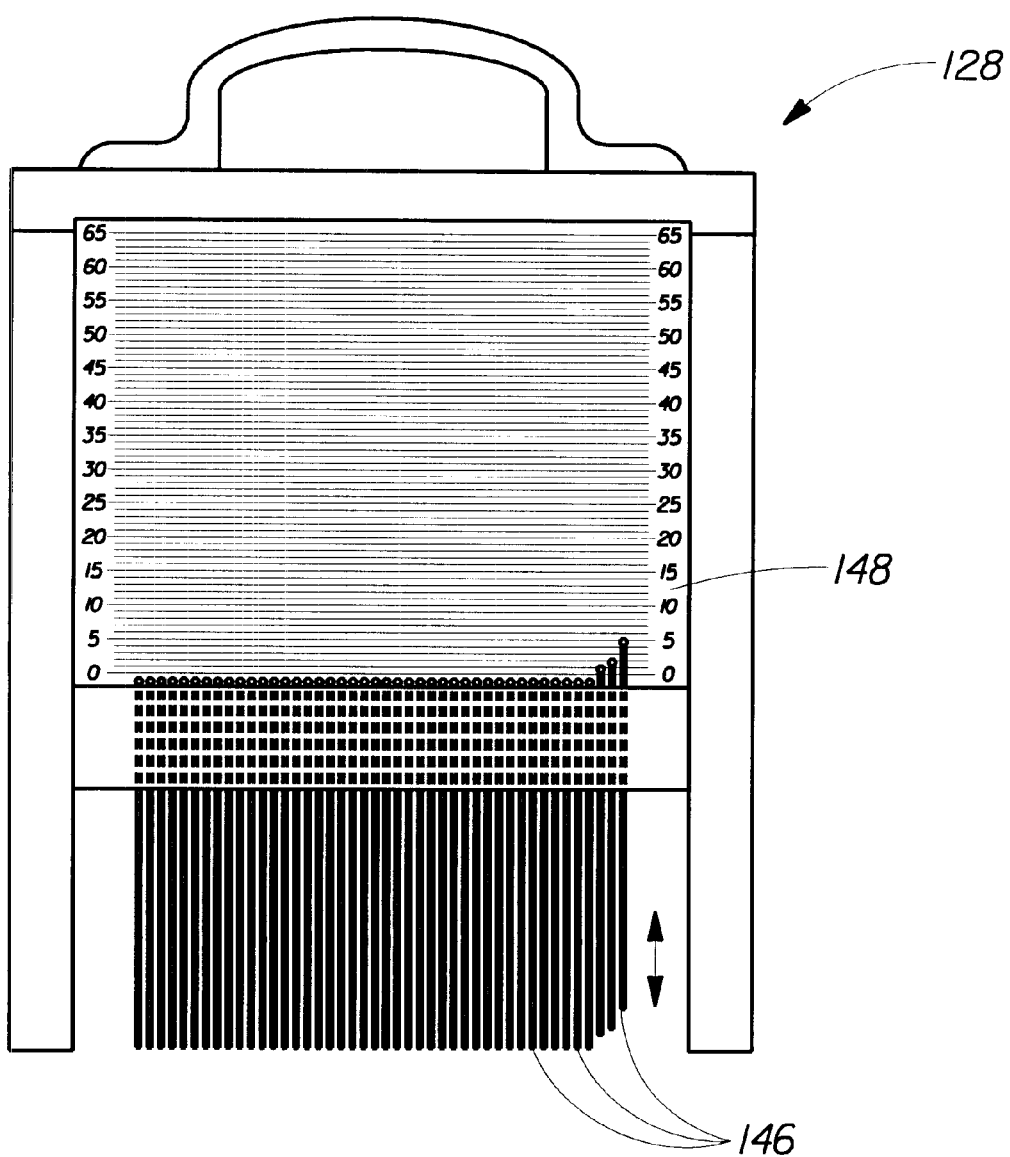
FIG. 14 is a front view of the Pin Chamber caliper measurement device used in the Lift Test.
Figure 15:
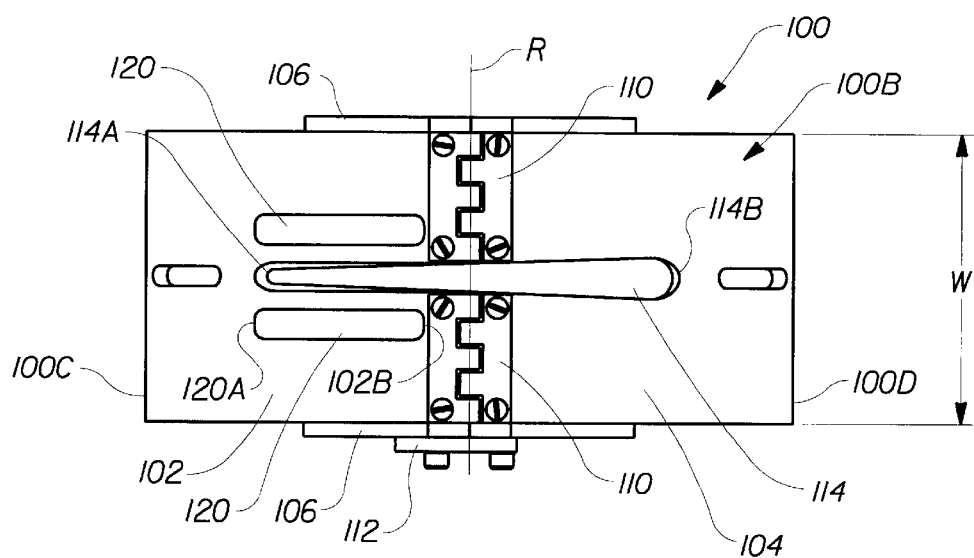
FIG. 15 is a bottom view of the Lift Test apparatus.
Figure 16:
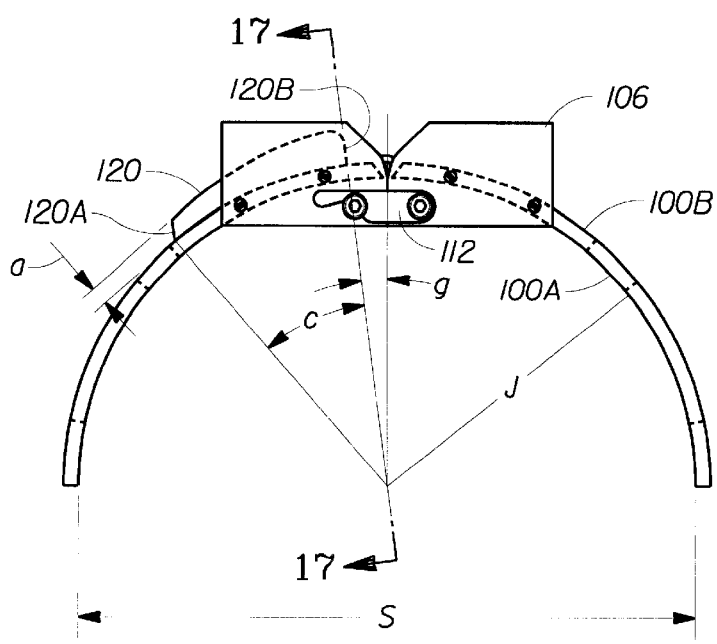
FIG. 16 is a side view of the Lift Test apparatus.

The PLEXIGLAS pieces include two identical ¼" thick arcuate pieces 102 and 104 which have a height H of 150 mm, a width W of 135 mm, a length S of 300 mm when assembled in an abutting relationship as shown in FIGS. 13–15, and a radius of curvature of the inner surface of the arcuate pieces, J (as shown in FIG. 15), of 150 mm. A pair of rectangular PLEXIGLAS support legs 106 are mounted on the sides of the arcuate PLEXIGLAS pieces as shown in FIG. 13. The support legs 106 are mounted perpendicularly to the arcuate pieces so that the bottom 108 of the arcuate pieces is held at least 20 mm above the table on which the test apparatus 100 is placed.

The arcuate pieces 102 and 104 are connected by a pair of hinges 110 that allow the arcuate pieces to open 90°. The arcuate pieces 102 and 104 are held together at the transverse centerline R of the test apparatus by a pivoting latch 112 when closed. The arcuate pieces have an 8⅜ inch (212 mm) long central longitudinally-oriented slit-like opening (or "slit") 114 (as measured along the curvature of the outside surface 100B of the arcuate pieces) that varies linearly in width from 6 mm at the portion 114A of the slit located nearest to the front of the portion 100C of the test apparatus (the portion of the apparatus that is intended to represent the front of the wearer's body) to 19 mm at the portion 114B of the slit located nearest to the rear 100D of the apparatus. The portions of the PLEXIGLAS surrounding the slit 114 are beveled at a 45° angle so that the slit is wider on the bottom surface 100B than on the top surface of the arcuate pieces. Both ends of the slit 114 are rounded.

The arcuate pieces have additional channels to the front and rear of the slit 114 which are oriented along the longitudinal centerline of the slit. These channels provide a mechanism within which the bolts holding the clamps 118 can slide to adjust the position of the clamps relative to the slit. The arcuate pieces 102 and 104 are provided with tape 116 which can be marked with indicia to indicate the proper position for clamping the ends of the sample in clamps 118.

The front arcuate piece 102 of the test apparatus is also provided with a pair of three-dimensionally curved PLEXIGLAS pieces 120 that are intended to represent the wearer's labia majora. The curved pieces 120 have the configuration shown in FIGS. 15–18 and the dimensions shown in Table 3 below. The curved pieces are centered about the slit and are spaced 36 mm apart (on center) as described in Table 3 and their rear end edges 120B are spaced from the rear end edge of the first arcuate plate 102 that is defined by the 8° angle g described in Table 3.

TABLE 3

Dimensions of Curved Pieces

| Dimension | Size (in mm) |
|---|---|
| a | 7 mm |
| b | 16 mm |
| c | 33 degrees |
| d | 16 mm |
| e | 6 mm (radius) |
| f | 36 mm |
| g | 8 degrees |
| Weights | Sufficient weight to place total weight of 391 grams on the sample (including weight of clamps (described below)). |
| Clamps | Spring-loaded, finger-operated 2 inch (5 centimeters) wide clamps (Boston No. 2 clips manufactured by Hunt Manufacturing Co., Statesville, N.C.) for attaching the weight to the sample. |
| Pin Chamber Caliper Measurement Device | Constructed according to Figure 14. |

Procedure

Figure 18:
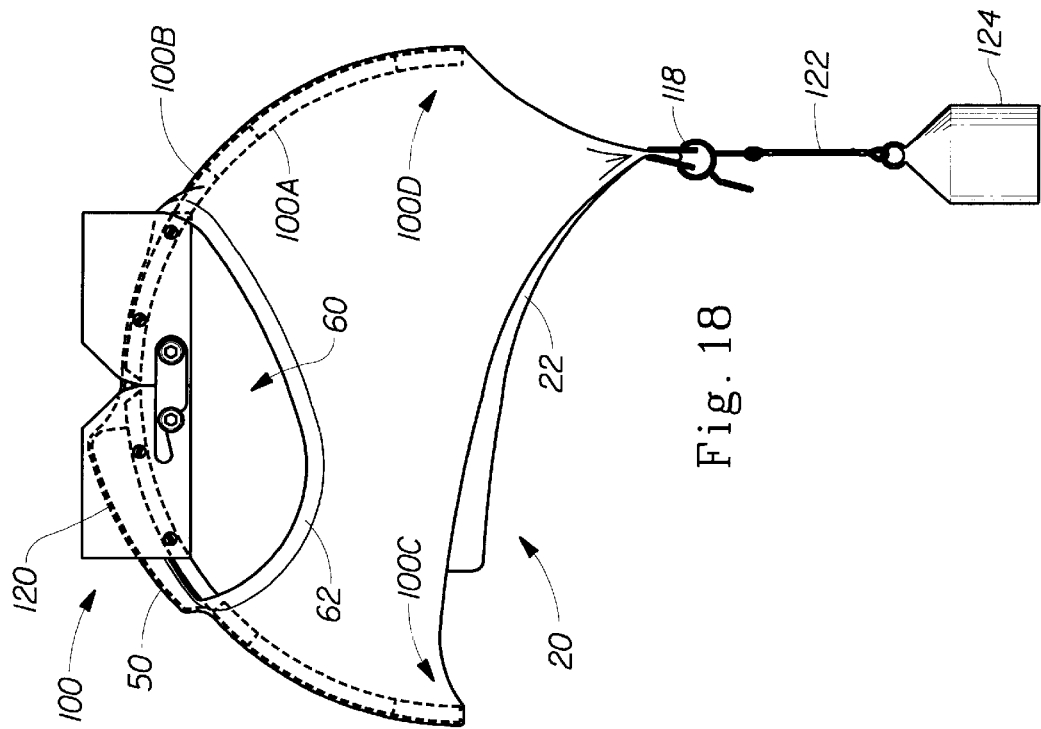
FIG. 18 is a side view of the calibration of the Lift Test apparatus showing a properly disposed undergarment.
Figure 17:
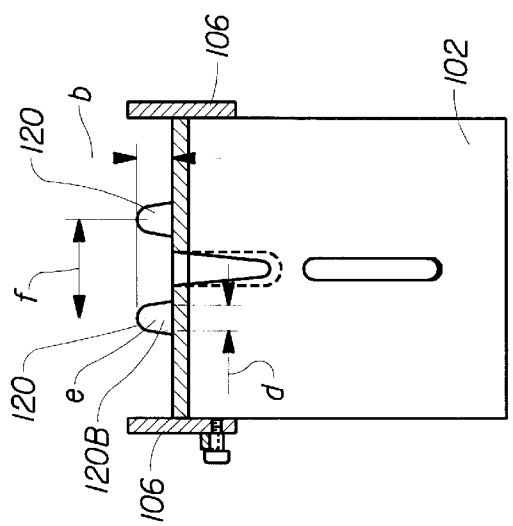
FIG. 17 is a cross-sectional view of one of the PLEXIGLAS plates used in the Lift Test apparatus as taken along line 17—17 of FIG. 16.

The undergarment is draped over the test apparatus 100 with the front of the waist opening directed toward the front portion of the test apparatus 100C. Insure that the support legs 106 are in the leg openings of the undergarment. The waistband is pulled over the front portion 100C and the rear portion 100D. Reposition the undergarment on the test apparatus 100 to insure it is centered thereon, insuring that the front edge of the crotch portion of the undergarment is in front of the front end edge of the curved pieces 120A (see 15 and 16). A properly disposed undergarment is shown in FIG. 18.

Weights 124 are hung from the clamp 118 at the end of the sample at the rear portion of the test apparatus. The weight is gently hung from the rear waist band of the sample undergarment by clamping clamp 118 thereto as it is laid over the waist edge of the test apparatus. The weight should not be dropped, nor should a sudden force be applied with the weight when the pad is hanging freely.

The weight on the end of the sample at the rear portion of the test device places a stretching force on the sample so that the sample tends to want to form a straight path between the clamps. At this point, the sample will move into as close contact within the slit as the sample is capable of achieving under the test conditions. Remove the weight after five seconds.

The test apparatus 100 is turned right side up so that it rests on its support legs 106. The Pin Chamber caliper measurement device is then used to measure the distance the sample rises within the slit from the outside surface 100B of the arcuate plates (the baseline).

The Pin Chamber 128 comprises a case with a plurality of narrow (1.1 mm diameter), spaced apart, vertically-oriented, lightweight (28.4 mg) pins 146 arranged in a row across the device. The pins are movable in the vertical direction. The Pin Chamber case has a glass window in the front and back so that the height of the pins can be observed when the Pin Chamber is in use. A ruler 148 marked in millimeter increments is provided along side of the pins prior to the placement of the sample on the test apparatus. The Pin Chamber is positioned over the test apparatus so that it straddles the test apparatus. A measurement to determine the distance the pins drop to the bottom surface of the arcuate plates is taken at each of the desired locations. These measurements serve as the baseline values for the test. The distance the pins drop above or below the baseline is then measured by gently lowering the pins with the sample in place. It should be noted that the slit is wide enough that several pins may drop between the edges of the slit at various locations. If that occurs, the reading taken is that of the highest pin.

The first measurement is taken at a point that is spaced 47 mm forward of the transverse centerline R of the test apparatus. This distance is intended to correspond with the labia area of wearer's body. (This 47 mm distance, and the following two distance measurements are measured along the curvature of the inside surface 100A of the test apparatus.) The second measurement is taken at a point that is spaced 17 mm to the rear of the transverse centerline of the test apparatus. This is intended to correspond with the wearer's perineum. The third measurement is taken at a point that is spaced 70 mm to the rear of the transverse centerline of the test apparatus. This is intended to correspond with the wearer's "gluteal groove". These values are recorded. The foregoing procedure is repeated for at least two representative samples. The measurements obtained are then averaged to provide a value for the Lift of the sample at each of the locations.

Stretch Modulus and Elastic Contractions

Intent

This method is intended to quantify a force comparable to the force exerted on a wearer's body by extensible materials that may be used in an undergarment over an extension range similar to that seen in the wear cycle of an undergarment.

Method

The method described in INDA (Association of Nonwoven Fabric Industry) Standard Test 110.1-92 is suitable. The following set up conditions are used:

Gage Length: 2 inches (5.08 centimeters)
Crosshead Speed: 10 inches/minute (25.4 centimeters/minute)
Tensile Testing Machine and Load Cell: Appropriate for expected force range, a Model 5564, available from Instron Corporation, Canton, Mass. is suitable
Sample Width: 1 inch (2.54 centimeters) For samples less than 1 inch (2.54 centimeters) wide, measure the sample width and adjust the measured force by the ratio of 1 inch (2.54 centimeters) to the measured width.
Sample Direction: Longitudinal stretch modulus samples are cut so the sample width is perpendicular to the longitudinal direction. Lateral stretch modulus samples are cut so the sample width is perpendicular to the lateral direction.
Sample Size: At least three samples per material tested Calculations $Force_0$: Force at start of data collection (grams/inch or grams/centimeter)
$Force_{25}$: Force at 25% elongation (grams/inch or grams/centimeter)
Elastic Contractions=$Force_{25}$
Stretch Modulus=$(Force_{25}-Force_0)/0.25$
Report the mean and standard deviation for elastic contractions (leg elastics only) and for stretch modulus

Body Contact Force

Introduction

This test is intended to determine the force exerted on a wearer's body by an elasticized undergarment. A commercially available mannequin is used to minimize error due to body dimension variation Apparatus Mannequin Suitable is a female, anatomically correct mannequin as is used to train medical personnel in catherization techniques. The mannequin has the following dimensions: thigh circumference—54 cm, waist circumference—92 cm, hip circumference—95 cm, andfront waist to back waist through groin—59 cm and is available from NASCO of Ft. Atkinson, Wis. as catalog number LF 856.

Pressure Sensors

Ultra thin piezo resistive pressure sensors (5mm×15mm, 0–10 mm Hg pressure range, with biomedical lead wires) as are available from Vistamedical, Ltd. of Winnipeg, Manitoba, Canada.

Computer

Pentium® based computer with 8MB RAM using the Windows 95® operating system. A laptop computer as is available from Dell Computer Corp. of Austin, Tex. as a model Latitude LM is suitable.

Electronic Interface Module

Model FSA-C-2-1.00 as is available from Vistamedical, Ltd. of Winnipeg, Manitoba, Canada.

Data Acquisition Software

FSA Version 3.1 as is available from Vistamedical, Ltd. of Winnipeg, Manitoba, Canada.

Method

1. Attach the leads from each sensor to the interface module according to the manufacturer's instructions. Calibrate each sensor by placing the sensor on an inflated air bladder (7.5 g/cm$^2$) and subjecting the sensor to known pressures (up to 7.5 g/cm$^2$) provided by a second air bladder that is disposed on the first bladder, the bladders being confined within a containment box as is supplied by the manufacturer. The FSA software acquires the signal produced and compares the signal with the calibration pressure which is entered by the operator. This comparison is used to build a calibration table which is stored as a file in the computer.

Figure 19A:
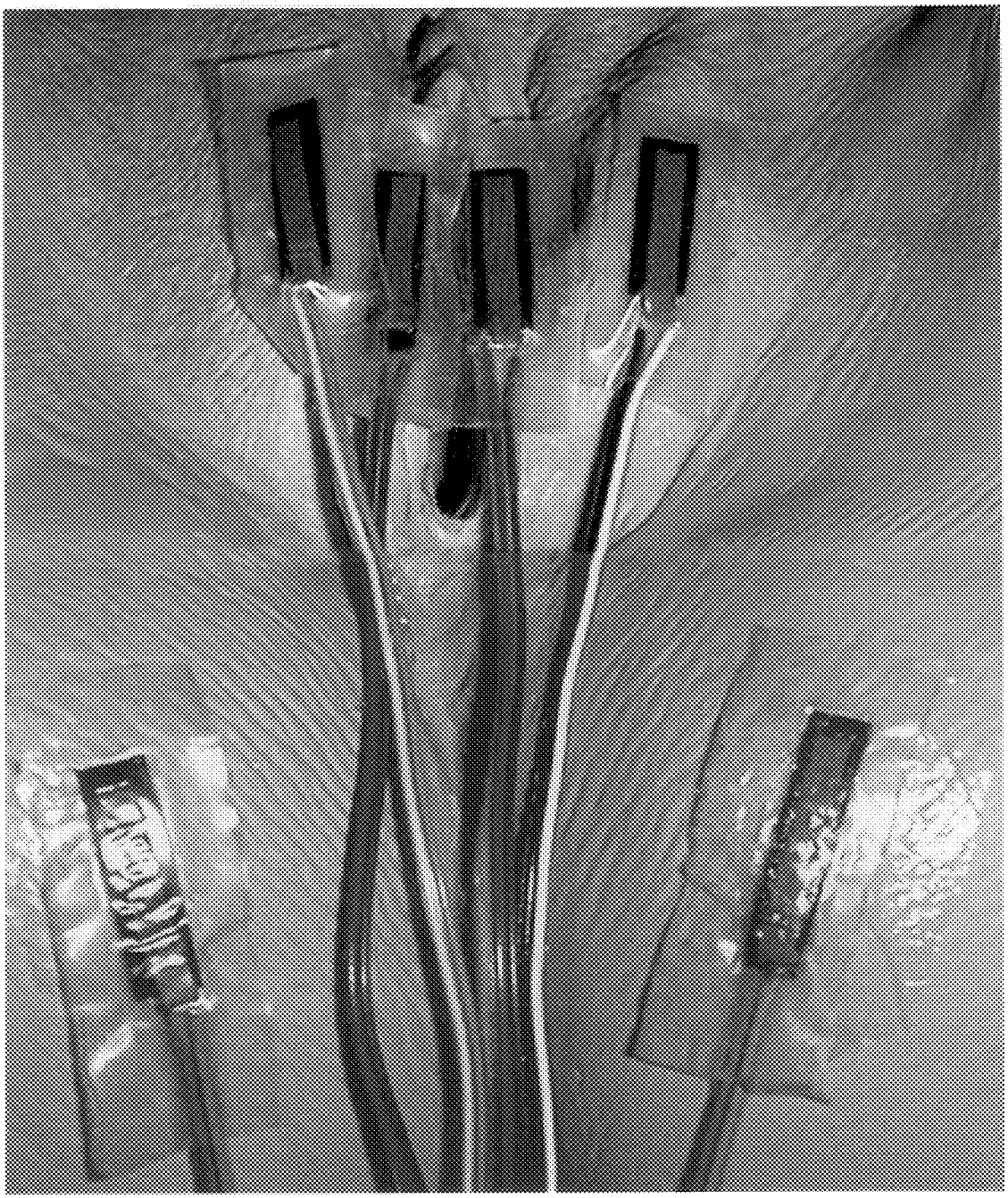
FIG. 19A is a photographic image of a rear view of the instrumented mannequin used in the body contact force test method.
Figure 19B:
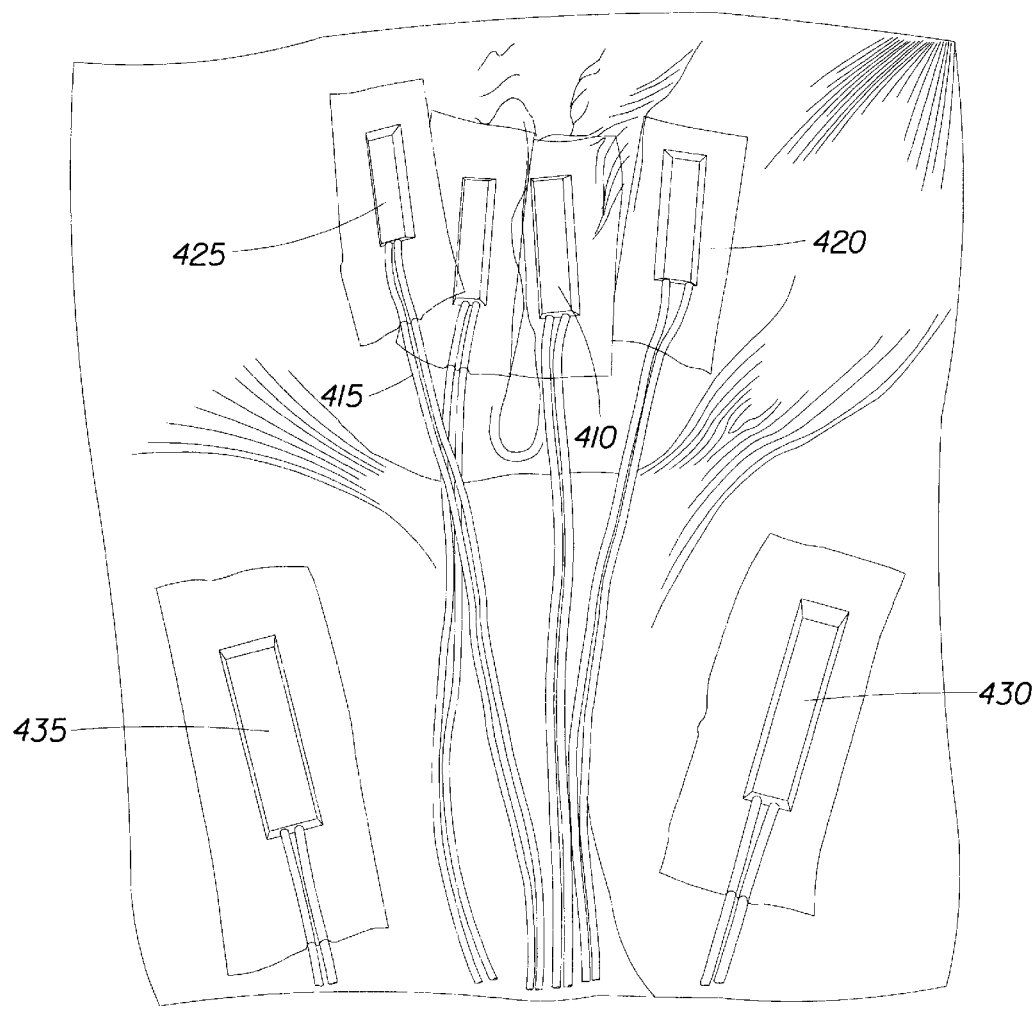
FIG. 19B is a schematic diagram of a rear view of the instrumented mannequin showing the placement of the force sensors. properly disposed undergarment.
Figure 20A:
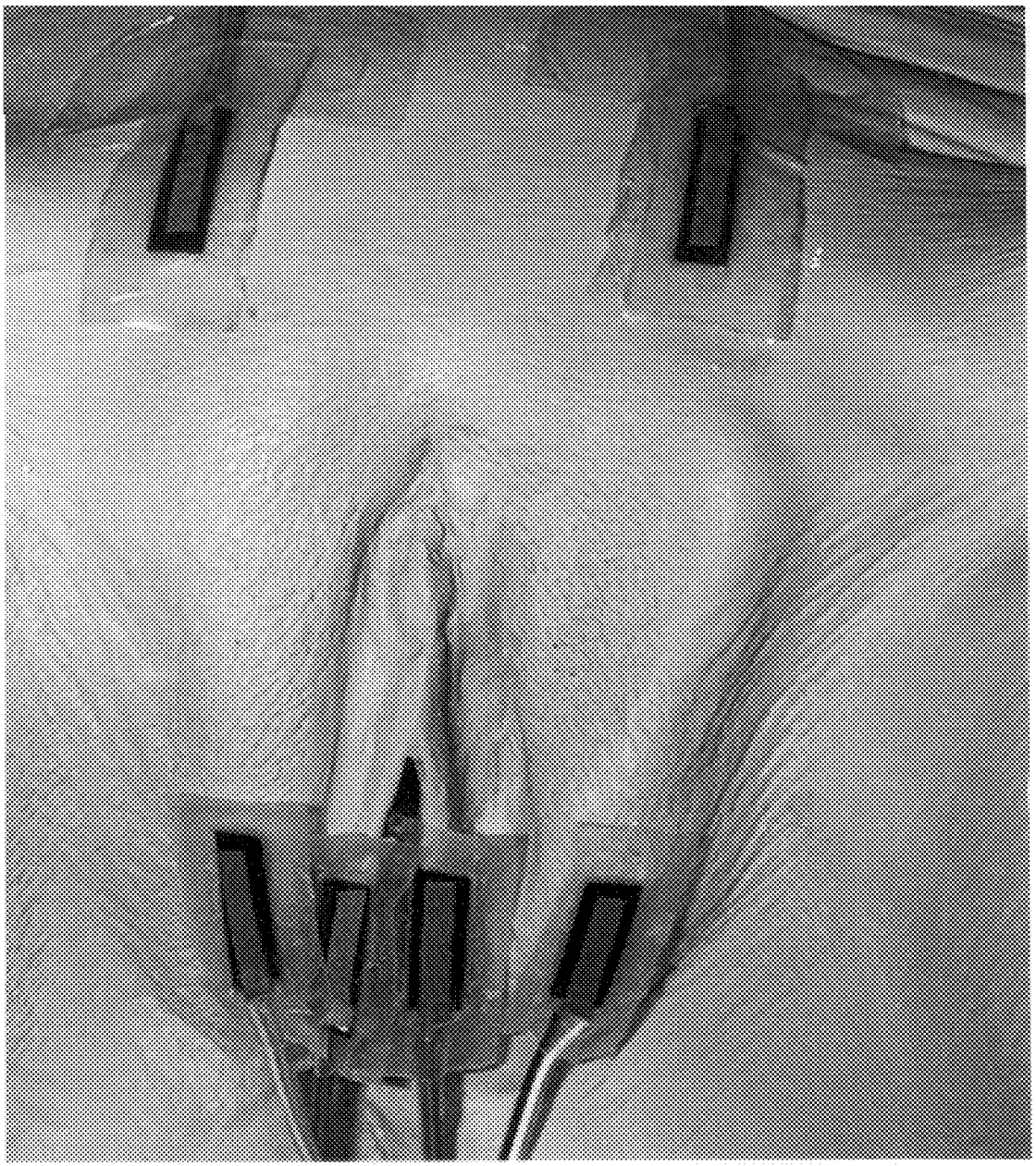
FIG. 20A is a photographic image of a front view of the instrumented mannequin used in the body contact force test method.
Figure 20B:
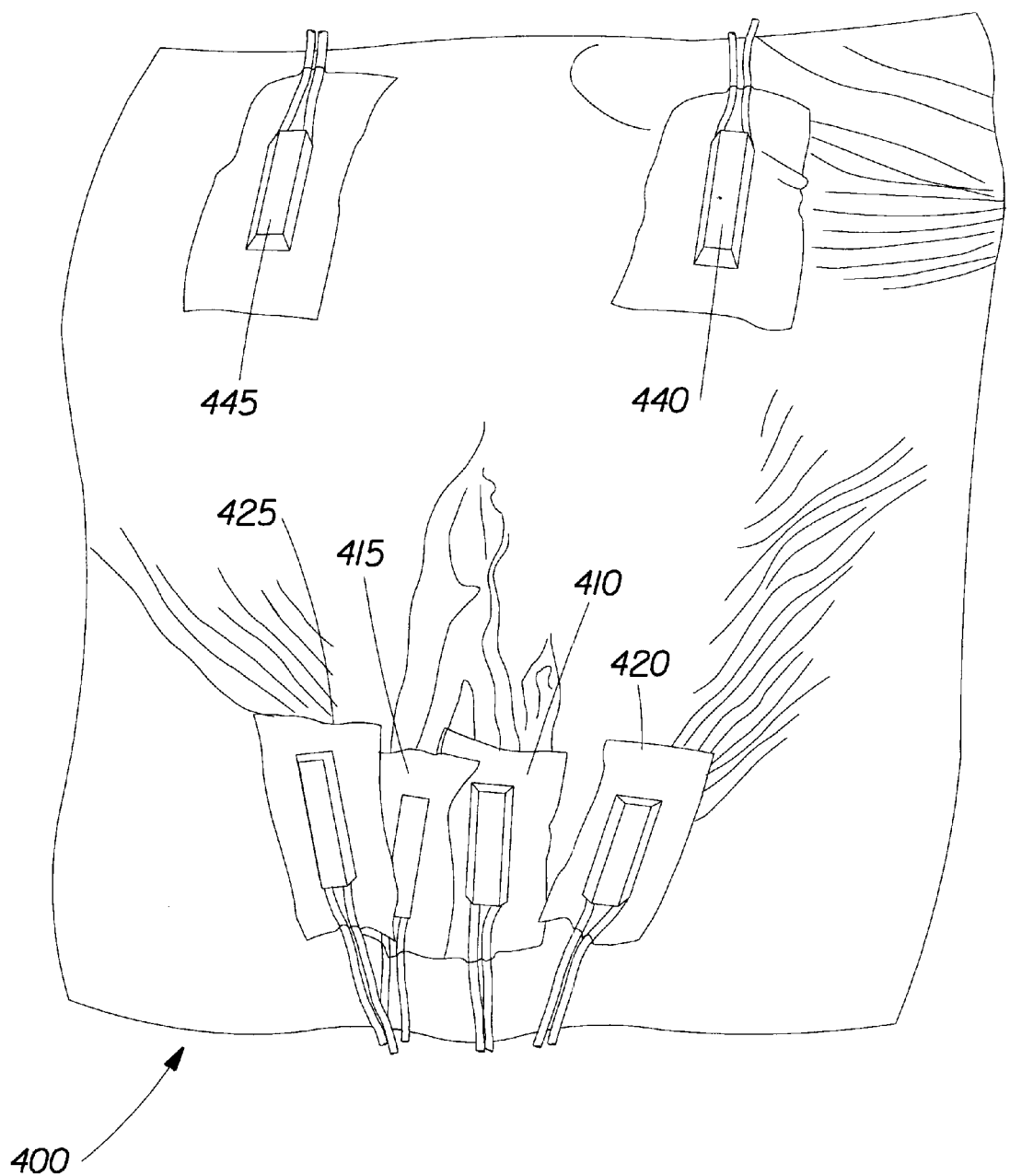
FIG. 20B is a schematic diagram of a front view of the instrumented mannequin showing the placement of the force sensors.

2. Attach the sensors to the mannequin 400 (FIGS. 19A, 19B, 20A. and 20B) using double sided transfer tape (available from 3M of St. Paul, Minn. as part no. 950). A first pair of sensors 410, 415 is placed on the apex of the manniquen's labia minora centered on the mannequin's urethra. A second pair of sensors 420, 425 is placed on the apex of the manniquen's labia majora at a position 6 mm anterior to sensors 410, 415 (FIGS. 19A, 19B). A third pair of sensors 430, 435 is placed on the surface of the manniquen's gluteaus at a position 32 mm posterior to the manniquen's posterior commissure of the labia minora (FIGS. 19A and 19B). The fourth and last set of sensors 440, 445 is placed on the surface of the manniquen's mons at a position 65 mm anterior to the center of the mannequin's urethra (FIGS. 20A and 20B).

3. Pull the garment on to the mannequin so it is smooth and symmetrically disposed about the manniquen's coronal centerline. The garment should be drawn up so as to be moderately tight. Reproducibility can be improved by recording the pressures at sensors 430, 435, 440, and 445 for a first garment and positioning subsequent garments so as to have as close to the same pressure as possible.

4. Acquire force data from sensors 410, 415, 420, and 425 using the interface module and software according to the manufacturer's instructions. A minimum of 4 samples should be evaluated. If desired, the acquired data can be exported into a spreadsheet file for further analysis by following instructions provided with the software.

5. Report mean and standard deviation for each sample. When samples are being compared, known statistical techniques (e.g. Analysis of Variance) can be used.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A garment for holding a disposable absorbent article in close bodily contact, said garment having a longitudinal centerline defining a longitudinal direction and a lateral centerline defining a lateral direction and a waist opening allowing entry thereto, said garment comprising a knit material and having:
   a front region;
   a rear region having at least two sections;
   a lifting member operatively associated with said rear region, said lifting member comprising at least one portion and being disposed in a symmetric relationship with respect to said longitudinal centerline, wherein said lifting member separates said rear region into said at least two sections;
   a crotch region disposed between and joined to said front region and said rear region;
   a pair of opposed leg openings having a periphery defined by said front region, said rear region and said crotch region; and
   a longitudinal stretch control member operatively associated with said lifting member, said longitudinal stretch control member being disposed along said longitudinal centerline in said crotch region, said longitudinal stretch control member has a rear end and said lifting member comprises a pair of opposed portions, each of said portions extending upward from said rear end of said lifting member toward said waistband and laterally outward at an acute angle with respect to said longitudinal centerline;
   said lifting member being integrally knit with said section of said rear region using a knitting pattern having less longitudinal stretch than a wholly plain knit pattern.

2. A garment according to claim 1 wherein said lifting member comprises a single portion disposed along said longitudinal centerline of said rear region.

3. A garment according to claim 2 wherein said garment further comprises a plurality of angled stretch control members disposed in said crotch region along said longitudinal stretch control member in a symmetric pattern, said angled stretch control members extending outward from said longitudinal stretch control member to said leg openings at an acute angle with respect to said longitudinal stretch control member.

4. A garment according to claim 3 wherein said longitudinal stretch control member is integrally knit with said crotch region, and said angled stretch control members are integrally knit with said crotch region.

5. A garment according to claim 4 wherein said longitudinal stretch control member comprises a knitting pattern having less longitudinal stretch than a wholly knit pattern.

6. A garment according to claim 1 wherein said longitudinal stretch control member provides a first body contact force and portions of said crotch region lying laterally outboard of said longitudinal stretch control member provide a second body contact force and the ratio of said first body contact force to said second body contact force is greater than 1:1.

7. A garment according to claim 6 wherein said first body contact force is greater than about 2.0 g/cm$^2$.

8. A garment according to claim 1 wherein said leg openings are provided with an elastic member disposed about said periphery which provides a third body contact force, said third body contact force being less than about 30 g/cm$^2$.

9. A garment according to claim 1 wherein each of said sections of said rear region has a longitudinal stretch modulus, said lifting member has a longitudinal stretch modulus, said crotch region has a longitudinal stretch modulus, and said longitudinal stretch control member has a longitudinal stretch modulus, said longitudinal stretch modulus of said lifting member being greater than said longitudinal stretch modulus of any of said sections and said longitudinal stretch modulus of said longitudinal stretch control member being greater than said longitudinal stretch modulus of said crotch region.

10. A garment according to claim 9 wherein said longitudinal stretch modulus of said longitudinal stretch control member is greater than said longitudinal stretch modulus of said lifting member.

11. A garment according to claim 9 wherein said longitudinal stretch modulus of said rear region is between about 1 gram per inch (0.4 grams/centimeter) and about 50 grams/inch (19.7 grams/centimeter).

12. A garment according to claim 9 wherein said longitudinal stretch modulus of said lifting member is between about 50 grams/inch (19.7 grams/centimeter) and about 110.0 grams/inch (43.3 grams/centimeter).

13. A garment according to claim 1 wherein said front region has a lateral stretch modulus, each of said portions of said rear region has a lateral stretch modulus, and said crotch region has a lateral stretch modulus, said lateral stretch modulus of said crotch region being less than or equal to said lateral stretch modulus of said front region, and less than or equal to said lateral stretch modulus of any of said portions of said rear region.

14. A garment according to claim 13 wherein said crotch region has a lateral stretch modulus between about 1 gram/inch (0.4 grams/centimeter) and about 50 grams /inch (19.7 grams/centimeter).

15. A garment according to claim 2 wherein said crotch region has a Lift of at least about 16 millimeters at Position 1 when measured according to the Lift Test.

16. A garment according to claim 2 wherein said crotch region has a Lift of at least about 25 millimeters at Position 2 when measured according to the Lift Test.

* * * * *